US005955583A

United States Patent [19]
Beavo et al.

[11] Patent Number: 5,955,583
[45] Date of Patent: Sep. 21, 1999

[54] ANTIBODIES TO CGMP-BINDING, CGMP-SPECIFIC PHOSPODIESTERASE

[75] Inventors: Joseph A. Beavo, Seattle, Wash.; Jackie D. Corbin, Nashville, Tenn.; Kenneth M. Ferguson, Bothell, Wash.; Sharron H. Francis, Nashville, Tenn.; Ann Kadlecek; Kate Loughney, both of Seattle, Wash.; Linda M. McAllister-Lucas, Nashville, Tenn.; William K. Sonnenburg, Mountlake Terrace, Wash.; Melissa K. Thomas, Boston, Mass.

[73] Assignees: ICOS Corporation, Bothell; Board of Regents of the University of Washington, Seattle, both of Wash.; Vanderbilt University, Nashville, Tenn.

[21] Appl. No.: 08/463,949

[22] Filed: Jun. 5, 1995

Related U.S. Application Data

[60] Division of application No. 08/250,847, May 27, 1994, which is a continuation-in-part of application No. 08/068, 051, May 27, 1993, abandoned.

[51] Int. Cl.$^6$ .............................. C07K 16/40; C12N 5/12
[52] U.S. Cl. .................................. 530/387.9; 530/387.3; 530/388.2; 530/388.85; 435/240.27
[58] Field of Search .............................. 424/133.1, 139.1, 424/146.1; 435/240.27; 530/387.3, 387.9, 388.26

[56] References Cited

FOREIGN PATENT DOCUMENTS

WO 92/18541  10/1992  WIPO.
WO 93/05182   3/1993  WIPO.

OTHER PUBLICATIONS

Thomas et al, J. Biol Chem 265: 14971–14978, 1990.
Sarada et al, Archives Biochem Biophys 215:183–198, 1982.
Mumby et al, J. Biol. Chem 257:13283–13290, 1982.
Riechmann et al., Nature 332:323–327, 1988.
Ausubel et al., *Current Protocols in Molecular Biology*, John Wiley & Sons, New York (1987) [Table of Contents].
Beavo et al., *Cyclic Nucleotide Phosphodiesterases: Structure, Regulation and Drug Action*, John Wiley & Sons, Chichester, UK (1990) [Table of Contents].
Bradford, "A Rapid and Sensitive Method for the Quantitation of Microgram Quantities of Protein Utilizing the Principle of Protein–Dye Binding", *Anal. Biochem.*, 72:248–254 (1976).
Charbonneau et al., "Identification of a Noncatalytic cGMP–Binding Domain Conserved in Both the cGMP–Stimulated and Photoreceptor Cyclic Nucleotide Phosphodiesterases", *Proc. Natl. Acad. Sci. USA*, 87:288–292 (1990).
Charbonneau, "Structure–Function Relationships Among Cyclic Nucleotide Phosphodiesterases", Chapter 11, pp. 267–296 in Beavo et al., *Cyclic Nucleotide Phosphodiesterases: Structure, Regulation and Drug Action*, John Wiley & Sons, Chichester, UK (1990).

Collins et al., "The Human β–Subunit of Rod Photoreceptor cGMP Phosphodiesterase: Complete Retinal cDNA Sequence and Evidence for Expression in Brain", *Genomics*, 13:698–704 (1992).
Coquil et al., "Characteristics of a New Binding Protein Distinct From the Kinase for Guanosine 3':5'–Monophosphate in Rat Platelets", *Biochim. Biophys. Acta*, 631:148–165 (1980).
Coquil et al., "Occurrence of the Methylisobutylxanthine–Stimulated Cyclic GMP Binding Protein in Various Rat Tissues", *Biochem. Biophys. Res. Commun.*, 127:226–231 (1985).
Davis et al., "Purification and Characterization of Guanosine 3':5'–Monophosphate–specific Phosphodiesterase from Guinea Pig Lung", *J. Biol. Chem.*, 252:4078–4084 (1977).
Dayhoff et al., "Establishing Homologies in Protein Sequences", *Methods Enzymol.*, 91:524–545 (1983).
Erickson et al., "Macromolecular X–Ray Crystallography and NMR as Tools for Structure–based Drug Design", *Ann. Rep. Med. Chem.*, 27:271–289 (1992).
Feinberg et al., "A Technique for Radiolabeling DNA Restriction Endonuclease Fragments to High Specific Activity", *Anal. Biochem.*, 137:266–267 (1984).
Feng et al., "Progressive Alignment and Phylogenetic Tree Construction of Protein Sequences", *Methods Enzymol.*, 183:375–387 (1990).
Flockhart et al., "Preparation of the Catalytic Subunit of cAMP–Dependent Protein Kinase", Chapter 12, pp. 209–215 in Marangos et al., *Brain Receptor Methodologies*, Part A, Academic Press, Orlando, Florida (1984).
Francis et al., "Cyclic GMP–Binding Cyclic GMP–Specific Phosphodiesterase from Lung", Chapter 5, pp. 117–140 in Beavo et al., *Cyclic Nucleotide Phosphodiesterases: Structure, Regulation and Drug Action*, John Wiley & Sons, Chichester, UK (1990).
Francis et al., "Characterization of a Novel cGMP Binding Protein from Rat Lung", *J. Biol. Chem.*, 255:620–626 (1979).
Francis et al., "Purification of cGMP–Binding Protein Phosphodiesterase from Rat Lung", *Methods Enzymol.*, 159:722–729 (1988).
Francis et al., "Cyclic Nucleotide Phosphodiesterases are Zinc Hydrolases as Indicated by Conserved Zinc–Binding Motifs, Specific Zinc Binding, and Zinc–supported Catalysis", *The FASEB J.*, 8: Abstract 2148 (May 15, 1994).

(List continued on next page.)

*Primary Examiner*—Marian C. Knode
*Assistant Examiner*—Nancy A. Johnson
*Attorney, Agent, or Firm*—Marshall, O'Toole, Gerstein, Murray & Borun

[57] ABSTRACT

The present invention provides novel purified and isolated nucleotide sequences encoding the cGMP-binding, cGMP-specific phosphodiesterase designated cGB-PDE. Antibodies to the cGMP-binding, cGMP-stimulated phosphodiesterase are disclosed. Also provided by the invention are methods and materials for the recombinant production of cGB-PDE polypeptide products and methods for identifying compounds which modulate the enzymatic activity of cGB-PDE polypeptides.

8 Claims, 10 Drawing Sheets

OTHER PUBLICATIONS

Hamet et al., "Cyclic GMP Binding and Phosphodiesterase-:Implication for Platelet Function", *Adv. Cyclic Nucleotide Protein Phosphorylation Res.,* 16:119–136 (1984).

LeTrong et al., "Amino Acid Sequence of the Cyclic GMP Stimulated Cyclic Nucleotide Phosphodiesterase from Bovine Heart", *Biochemistry,* 29:10280–10288 (1990).

Li et al., "Bovine Cone Photoreceptor cGMP Phosphodiesterase Structure Deducted from A cDNA Clone", *Proc. Natl. Acad. Sci. USA,* 87:293–297 (1990).

Lipkin et al., "β–Subunit of Bovine Rod Photoreceptor cGMP Phosphodiesterase", *J. Biol. Chem.,* 265:12955–12959 (1990).

Martins et al., "Purification and Characterization of a Cyclic GMP–Stimulated Cyclic Nucleotide Phosphodiesterase from Bovine Tissues", *J. Biol. Chem.,* 257:1973–1979 (1982).

Matsudaira, "Sequence from Picomole Quantities of Proteins Electroblotted Onto Polyvinylidene Difluoride Membranes", *J. Biol. Chem.,* 262:10035–10038 (1987).

McAllister–Lucas et al., "Mutagenesis of a Lung cGMP–Specific Phosphodiesterase Provides Evidence for Two Distinct sites for Allosteric cGMP–Binding, with an essential Aspartic Acid at Each Site", *The FASEB J., Abstract* 2149 (Mar. 15, 1994).

Murray et al., "Inhibitors of Cyclic Nucleotide Phosphodiesterases as Therapeutic Agents", *Biochem. Soc. Trans.,* 20(2):460–464 (1992).

Oskenberg et al., "A Single Amino–Acid Difference Confers Major Pharmacological Variation Between Human and Rodent 5–HT$_{1B}$ Receptors", *Nature,* 360:161–163 (1992).

Ovchinnikov et al., "Cyclic GMP Phosphodiesterase from Cattle Retina", *FEBS Lett.,* 204:288–292 (1986).

Ovchinnikov et al., "Cyclic GMP Phosphodiesterase From Bovine Retina", *FEBS Lett.,* 223:169–173 (1987).

Price et al., "Expression of Heterologous Protiens in *Saccharomyces cerevisiae* Using the ADH2 Promoter", *Meth Enzymol.,* 185: 308–318 (1990).

Prpic et al., "Separation and Assay of Phosphodiesterase Isoforms in Murine Peritoneal Macrophages Using Membrane Matrix DEAE Chromatography and [$^{32}$P]cAMP", *Anal Biochem,* 208: 155–160 (1993).

Reeves et al., Cardiac Phosphodiesterases and the Functional Effects of Selective Inhibition, Chapter 12, pp. 300–316 in Beavo et al., *Cyclic Nucleotide Phosphodiesterases: Structure, Regulation and Drug Action,* John Wiley & Sons, Chichester, UK (1990).

Sonnenburg et al., "Molecular Cloning of a Cyclic GMP–Stimulated Cyclic Nucleotide Phosphodiesterase cDNA", *J. Biol. Chem.,* 266:17655–17661 (1991).

Thomas et al., "Substrate– and Kinase–directed Regulation of Phosphorylation of a cGMP–binding Phosphodiesterase by cGMP", *J. Biol. Chem.,* 265:14971–14978 (1990).

Thomas et al., "Characterization of a Purified Bovine Lung cGMP–Binding cGMP Phosphodiesterase", *J. Biol. Chem.,* 265:14964–14970 (1990).

Valle and Auld. "Zinc Coordination, Function, and Structure of ZInc Enzymes and Other Proteins", *Biochem.,* 29: 5647–5659 (1990).

Wilbur et al., "Rapid Similarity Searches of Nucleic Acid and Protein Data Banks", *Proc. Natl. Acad. Sci. USA,* 80:726–730 (1983).

| | | | | | |
|---|---|---|---|---|---|
| cGB-PDE | FQMKHEVLCK | WILSVKKNYR | K.NVAYHNWR | HAFNTAQCMF | AALKAGKIQK | 626 |
| ROS-α | FHIPQEALVR | FMYSLSKGYR | R..ITYHNWR | HGFNVGQTMF | SLLVTGKLKR | 582 |
| ROS-β | FQIPQEVLVR | FLFSVSKGYR | R..ITYHNWR | HGFNVAQTMF | TLLMTGKLKS | 580 |
| CONE-α′ | FKVPVEVLTR | WMTYVRKGYR | A..VTYHNWR | HGFNVGQTMF | TLLMTGRLKK | 580 |
| cGS | YKIDCPTLAR | FCLMVKKGYR | D.P.PYHNWM | HAFSVSHFCY | LLYKNLELTN | 659 |
| 61 kCaM | FKIPVSCLIA | FAEALEVGYS | KYKNPYHNLI | HAADVTQTVH | YIMLHTGIMH | 242 |
| 63 kCaM | FKIPTVFLMT | FLDALETGYG | KYKNPYHNQI | HAADVTQTVH | CFLLRTGMVH | 244 |
| RatDunce | FQIPADTLLR | YLLTLEGHYH | S.NVAYHNSI | HAADVVQSAH | VLLGTPALEA | 125 |
| DrosDunce | .MIPPKTFLN | FMSTLEDHYV | K.DNPFHNSL | HAADVTQSTN | VLLNTPALEG | 48 |
| Conserved | ---------- | ---*------ | -------Y-- | ------*-- | -*-------- | |

| | | | | | |
|---|---|---|---|---|---|
| cGB-PDE | RLTDLEILAL | LIAALSHDLD | HRGVNNSYIQ | RSEHPLAQLY | CH..SIMEHH | 674 |
| ROS-α | YFTDLEALAM | VTAAFCHDID | HRGTNNLYQM | KSQNPLAKLH | GS...SILERH | 630 |
| ROS-β | YYTDLEAFAM | VTAGLCHDID | HRGTNNLYQM | KSQNPLAKLH | GS...SILERH | 628 |
| CONE-α′ | YYTDLEAFAM | LAAAFCHDID | HRGTNNLYQM | KSTSPLARLH | GS...SILERH | 628 |
| cGS | YLEDMEIFAL | FISCMCHDLD | HRGTNNSFQV | ASKSVLAALY | SSEGSVMERH | 709 |
| 61 kCaM | WLTELEILAM | VFAAAIHDYE | HIGTTNNFHI | QTRSDVAILY | .NDRSVLENH | 291 |
| 63 kCaM | CLSEIEVLAI | IFAAAIHDYE | HIGTTNSFHI | QTKSEQAILY | .NDRSVLENH | 293 |
| RatDunce | VFTDLEVLAA | IFACAIHDVD | HPGVSNQFLI | NTNSELALMY | .NDSSVLENH | 174 |
| DrosDunce | VFTPLEVGGA | LFAACIHDVD | HPGLTNQFLV | NSSSELALMY | .NDESVLENH | 97 |
| Conserved | -----E---- | ---------- | H-G--N-*-- | -----A--- | ----S--E-H | |

FIGURE 1A

```
cGB-PDE     HFDQCLMILN SPGNQILSGL SIEEYKTTLK IIKQAILATD LALYIKRRGE  724
ROS-α       HLEFGKTLLR DESLNIFQNL NRRQHEHAIH MMDIAIIATD LALYCKKRTM  680
ROS-β       HLEFGKFLLS EETLNIYQNL NRRQHEHVIH LMDIAIIATD LALYFKKRTM  678
CONE-α'     HLEYSKTLLQ DESLNIFQNL NKRQYETVIH LFEVAIIATD LALYFKKRTM  678
cGS         HFAQAIAILN THGCNIFDHF SRKDYQRMLD LMRDIILATD LAHHLRIFKD  748
61 kCaM     HVSAAYRLMQ EEEMNVLINL SKDDWRDLRN LVIEMVLSTD MSGHFQQIKN  326
63 kCaM     HISSVFRMMQ DDEMNIFINL TKDEFVELRA LVIEMVLATD MSCHFQQVKS  328
Ratdunce    HLAVGFKLLQ GENCDIFQNL STKQKLSLRR MVIDMVLATD MSKHMSLLAD  220
Drosdunce   HLAVAFKLLQ NQGCDIFCNM QKKQRQTLRK MVIDIVLSTD MSKHMSLLAD  143
Conserved   H--------- ---------- ---------- --------TD --*-*----- cGB-PDE     FFELIMKN..  ........QF NLEDPHQKEL FLAMLMTACD LSAITKPWPI  764
ROS-α       FQKIVDQSKT  YETQQEWTQY MMLDQTRKEI VMAMMMTACD LSAITKPWEV  730
ROS-β       FQKIVDESKN  YEDRKSWVEY LSLETTRKEI VMAMMMTACD LSAITKPWEV  728
CONE-α'     FQKIVDACEK  METEEEAIKY VTIDPTKKEI IMAMMMTACD LSAITKPWEV  728
cGS         LQKMAE....  ........VGY DRTNKQHHSL LLCLLMTSCD LSDQTKGWKT  798
61 kCaM     IRNSLQQPEG  L......... ......DKAK TMSLILHAAD ISHPAKSWKL  376
63 kCaM     MKTALQQLER  I......... ......DKSK ALSLLLHAAD ISHPTKQWSV  378
Ratdunce    LKTMVETKKV  T....SLGVL LLDNYSDRIQ VLQSLVHCAD LSNPAKPLPL  270
Drosdunce   LKTMVETKKV  A....GSGVL LLDNYTDRIQ VLENLVHCAD LSNPTKPLPL  193
Conserved   *--------- ---------- ---------*- -------D -S-K----
```

FIGURE 1B

| | | | | | |
|---|---|---|---|---|---|
| cGB-PDE | QQRIAELVAT | EFFDQGDRER | KELNIEPADL | MNREKKNKIP | SMQVGFID... | 812 |
| ROS-α | QSKVALLVAA | EFWEQGDLER | TVLQQNPIPM | MDRNKADELP | KLQVGFID... | 778 |
| ROS-β | QSKVALLVAA | EFWEQGDLER | TVLDQQPIPM | MDRNKAAELP | KLQVGFID... | 776 |
| CONE-α | QSQVALLVAN | EFWEQGDLER | TVLQQQPIPM | MDRNKKDELP | KLQVGFID... | 776 |
| cGS | TRKIAELIYK | EFFSQGDLEK | A.MGNRPMEM | MDREKAY.IP | ELQISFME.. | 844 |
| 61 kCaM | HHRWTMALME | EFFLQGDKEA | EL..GLPFSP | LCDRKSTMVA | QSQIGFID.. | 422 |
| 63 kCaM | HSRWTKALME | EFFRQGDKEA | EL..GLPFSP | LCDRTSTLVA | QSQIGFID.. | 424 |
| RATDUNCE | YRQWTERIMA | EFFQQGDRER | ES..GLDISP | MCDKHTASVE | KSQVGFID.. | 316 |
| DROSDUNCE | YKRWVALLME | EFFLQGDKER | ES..GMDISP | MCDRHNATIE | KSQVGFID.. | 239 |
| CONSERVED | *-----**- | EF--QGD-E- | ---------- | ---------- | --Q--F---  | |

FIGURE 1C

```
cGB-PDE    LLELVKDISS  HLDVTALCHK  IFLHIHGLIS  ADRYSLFLVC  EDSSNDKFLI   188
cGS        ILQLCGELYD  .LDASSLQLK  VLQYLQQETQ  ASRCCLLLVS  EDN..LQ.LS   245
CONE-α'    LLEVL..LEE  AGSVELAAHR  ALQRLAQLLQ  ADRCSMFLCR  ARNGTPE.VA   106
ROS-β      LFELVQDMQE  NVNMERVVFK  ILRRLCSILH  ADRCSLFMYR  QRNGVAE.LA   107
ROS-α      ...LLRDFQD  NLQAEKCVFN  VMKKLCFLLQ  ADRMSLFMYR  ARNGIAE.LA   109
CONSERVED  ----------  ----------  ----------  ---A-R----  ---------- cGB-PDE    SRLFDVAEGS  TLEE...ASN  NCIRLEWNKG  IVGHVAAFGE  PLNIKDAYED   237
cGS        CKVIG...DK  VLEE......  .EISFPLTTG  RLGQVVEDKK  SIQLKDLTSE   292
CONE-α'    SKLLDVTPTS  KFEDNLVVPD  REAVFPLDVG  IVGWVAHTKK  TFNVPDVKKN   154
ROS-β      TRLFSVQPDS  VLEDCLVPPD  SEIVFPLDIG  VVGHVAQTKK  MVNVQDVMEC   155
ROS-α      TRLFNVHKDA  VLEECLVAPD  SEIVFPLDMG  VVGHVALSKK  IVNVPNTEED   157
CONSERVED  ----------  ---E------  --------G-  ---G-V----  ---------- cGB-PDE    PRFNAEVDQI  TGYKTQSILC  MPIKNHR.EE  VVGVAQAINK  KSGNGGTFTE   287
cGS        DM..QQLQSM  LGCEVQAMLC  VPVISRATDQ  VVALACAFNK  ..LGGDLFTD   342
CONE-α'    SHFSDFMDKQ  TGYVTRNLLA  TPIV..MGKE  VLAVFMAVNK  ..VDASEFSK   204
ROS-β      PHFSSFADEL  TDYVTRNILA  TPIM..NGKD  VVAVIMAVNK  ..LDGPCFTS   205
ROS-α      EHFCDFVDTL  TEYQTKNILA  SPIM..NGKD  VVAIIMAVNK  ..VDGPHFTE   207
CONSERVED  ----------  ------L---  ----P-----  V-----A-NK  ------F---
```

FIGURE 2A

```
cGB-PDE     KDEKDFAAYL AFCGIVLHNA QLYETSLLEN KRNQVLLDLA SLIFEEQQSL  337
cGS         QDEHVIQHCF HYTSTVLTST LAFQKEQKLK CECQALLQVA KNLFTHLDDV  390
CONE-α'     QDEEVFSKYL SFVSIILKLH HTNYLYNIES RRSQILMWSA NKVFEELTDV  252
ROS-β       EDEDVFLKYL NFGTLNLKIY HYSYLHNCET RRGQVLLWSA NKVFEELTDI  253
ROS-α       NDEEILLKYL NFANLIMKVF HLSYLHNCET RRGQILLWSG SKVFEELTDI  255
CONSERVED   -DE------- ---------- ---------- ---Q---L-- -----F--- cGB-PDE     EVILKKIAAT IISFMQVQKC TIFIVD.EDC SDSFSSVFHM ECEELEKSSD  386
cGS         SVLLQEIITE ARNLSNAEIC SVFLID...Q NELVAKVFDG GVLEDESY..  409
CONE-α'     ERQFHKALYT VRTYLNCERY SIGLLDMTKE KEFY.DEWPV KPGEVEPYKG  301
ROS-β       ERQFHKAFYT VRAYLNCDRY SVGLLDMTKE KEFF.DVWPV LMGEAQAYSG  302
ROS-α       ERQFHKALYT VRAFLNCDRY SVGLLDMTKQ KEFF.DVWPV LMGEAPPYAG  304
CONSERVED   ---------- ---------- ----D----- ---------- ---E------ cGB-PDE     TLTRE..... .......... ..RDANRINY MYAQYVKNTM               409
cGS         .......... .......... .PADQ..... GIAGHVATTG               459
CONE-α'     PKTPDGREVI FYKIIDYILH .EIRI..... PPMDHWTLIS GLPTYVAENG      351
ROS-β       PRTPDGREIL FYKVIDYILH GKEEIKVIPT PPADHWALAS GLPTYVAESG      352
ROS-α       PRTPDGREIN FYKVIDYILH GKEDIKVIPS PPPDHWALVS GLPTYVAQNG      354
CONSERVED   ---------- ---------- ---------- ---D------ -----V----
```

FIGURE 2B

```
cGB-PDE     EPLNIPDVSK  DKRFPWTNEN  MGNINQQCIR  SLLCTPIKNG  KKNKVIGVCQ  459
CGS         QILNIPDAYA  HPLFY...RGV DDSTGRF.TR  NILCFPIKN.  ENQEVIGVAE  499
CONE-α'     FICNMLNAPA  DEYFTFQKGP  VDETGWV.IK  NVLSLPIVN.  KKEDIVGVAT  399
ROS-β       FICNIMNAPA  DEMFNFQEGP  LDDSGWI.VK  NVLSMPIVN.  KKEEIVGVAT  400
ROS-α       LICNIMNAPS  EDFFAFQKEP  LDESGWM.IK  NVLSMPIVN.  KKEEIVGVAT  402
CONSERVED   ------N---  ------F---  ----------  --L--PI-N-  ------GV-- cGB-PDE     LVNKMEETTG  KVKAFNRNDE  QFLEAFVIFC  GLGIQNTQMY  EAVERAMAKQ  509
CGS         LVNKING...  ..PWFSKFDE  DLATAFSIYC  GISIAHSLLY  KKVNEAQYRS  541
CONE-α'     FYNRKDG...  ..KPFDEYDE  HIAETLTQFL  GWSLLNTDTY  EKMNKLENRK  441
ROS-β       FYNRKDG...  ..KPFDEQDE  VLMESLTQFL  GWSVLNTDTY  DKMNKLENRK  442
ROS-α       FYNRKDG...  ..KPFDEMDE  TLMESLAQFL  GWSVLNPDTY  ELMNKLENRK  444
CONSERVED   ------N---  ------F---  -------DE   G-------Y   ---------- cGB-PDE     MVTLEVLSYH  ASAAEEE                                         526
CGS         HLANEMMMYH  MKVSDDE                                         561
CONE-α'     DIAQEMLMNH  TKATPDE                                         461
ROS-β       DIAQDMVLYH  VRCDREE                                         462
ROS-α       DIFQDMVKYH  VKCDNEE                                         464
CONSERVED   ---------H  ------E
```

FIGURE 2C

```
CGB-PDE      A   EPLNIKDAYEDPRF...NAEVDQITGYKTQSILCMPIKMH.REEVVGVAQAIN.KKSGN
ROS-α        A   KIVNVPNTEEDEHF...CDFVDTLTEYQTKNILASPIMNG.K.DVVAIIMAVN.KVDGP
ROS-β        A   KMVNVQDVMECPHF...SSFADELTDYVTRNILATPIMNG.K.DVVAVIMAVN.KLDGP
CONE-α'      A   KTFNVPDVKKNSHF...SDFMDKQTGYVTRNILATPIVMG.K.EVLAVFMAVN.KVDAS
CGS          A   KSIQLKDLTSEDM....QQLQSMLGCEVQAMLCVPVISRATDQVVALACAFN.KLGGD
CGB-PDE      B   EPLNIPDVSKDKRFPWTNENMGNINQQCIRSLLCTPIKNGKKNKVIGVCQLVN.KMEET
ROS-α        B   LICNIMNAPSEDFFAFQKEPLDE.SGWMIKNVLSMPIVNK.KEEIVGVATFYNRKDGKP
ROS-β        B   FICNIMNAPADEMFNFQEGPLDD.SGWIVKNVLSMPIVNK.KEEIVGVATFYNRKDGKP
CONE-α'      B   FICNMLNAPADEYFTFQKGPVDE.TGWIVKNVLSLPIVNK.KEDIVGVATFYNRKDGKP
CGS          B   QILNIPDAYAHPLF...YRGVDDSTGFRTRNILCFPIKNE.NQEVIGVAELVN.KINGP
Conserved        ---*----------------------------L--P*----*****-----N-K---

CGB-PDE      A   GG...TFTEKDEKDFAAYLAFCGIVLHMAQL.YE
ROS-α        A   ......HFTENDEEILLKYLNFANLIMKVFHLSY.
ROS-β        A   ......CFTSEDEDVFLKYLNFGTLNLKIYHLSY.
CONE-α'      A   ......EFSKQDEEVFSKYLSFVSIILKLHHTNY.
CGS          A   ......LFTDQDEHVIQHCFHYTSTVL.TSTLAFQ
CGB-PDE      B   TGKVKAFNRNDEQFLEAFVIFCGLGIQNTQM.YE
ROS-α        B   ......FDEMDETLMESLAQFLGWSV.LNPDTYE
ROS-β        B   ......FVEQDEVLMESLTQFLGWSV.LNTDTYD
CONE-α'      B   ......FDEYDEHIAETLTQFLGWSL.LNTDTYE
CGS          B   ......WFSKFDEDLATAFSIYCGISI.AHSLLYK
Conserved        -----F----DE-----------------*---*-
```

FIGURE 3

```
                         SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
           (A) LENGTH: 20 amino acids
           (B) TYPE: amino acid
           (D) TOPOLOGY: linear (ii) MOLECULE TYPE: peptide (xi) SEQUENCE DESCRIPTION: SEQ ID NO:1:

Arg Glu Xaa Asp Ala Asn Arg Ile Asn Tyr Met Tyr Ala Gln Tyr Val
   1               5                  10                  15

Lys Asn Thr Met
               20

(2) INFORMATION FOR SEQ ID NO:2:

(i) SEQUENCE CHARACTERISTICS:
           (A) LENGTH: 9 amino acids
           (B) TYPE: amino acid
           (D) TOPOLOGY: linear (ii) MOLECULE TYPE: peptide (xi) SEQUENCE DESCRIPTION: SEQ ID NO:2:

Gln Ser Leu Ala Ala Ala Val Val Pro
   1               5

(2) INFORMATION FOR SEQ ID NO:3:

(i) SEQUENCE CHARACTERISTICS:
           (A) LENGTH: 8 amino acids
```

(B) TYPE: amino acid
        (D) TOPOLOGY: linear (ii) MOLECULE TYPE: peptide (xi) SEQUENCE DESCRIPTION: SEQ ID NO:3:

Phe Asp Asn Asp Glu Gly Glu Gln
1               5

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTYGAYAAYG AYGARGGNGA RCA                                           23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:5:

AARCTRTTRC TRCTYCCNCT YGT                                           23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AAYTAYATGT AYGCNCARTA YGT                                           23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:7:

TTRATRTACA TRCGNGTYAT RCA                                           23

(2) INFORMATION FOR SEQ ID NO:8:

(i) SEQUENCE CHARACTERISTICS:
        (A) LENGTH: 36 base pairs
        (B) TYPE: nucleic acid (C) STRANDEDNESS: single
(D) TOPOLOGY: linear (ii) MOLECULE TYPE: DNA (iv) ANTI-SENSE: YES (xi) SEQUENCE DESCRIPTION: SEQ ID NO:8:

```
TTRATRTACA TRCGNGTYAT RCANTTYTTR TGNTAC                              36
```

(2) INFORMATION FOR SEQ ID NO:9:

(i) SEQUENCE CHARACTERISTICS:
        (A) LENGTH: 4474 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 99..2723

(xi) SEQUENCE DESCRIPTION: SEQ ID NO:9:

```
GGGAGGGTCT CGAGGCGAGT TCTGCTCCTC GGAGGGAGGG ACCCCAGCTG GAGTGGAAAA          60

CCAGCACCAG CTGACCGCAG AGACACGCCG CGCTGATC ATG GAG AGG GCC GGC             113
                                        Met Glu Arg Ala Gly
                                          1               5

CCC GGC TCC GCG CGG CCG CAA CAG CAA TGG GAC CAG GAC TCG GTC GAA          161
Pro Gly Ser Ala Arg Pro Gln Gln Gln Trp Asp Gln Asp Ser Val Glu
             10                  15                  20

GCG TGG CTG GAC GAT CAC TGG GAC TTT ACC TTC TCT TAC TTT GTT AGG          209
Ala Trp Leu Asp Asp His Trp Asp Phe Thr Phe Ser Tyr Phe Val Arg
         25                  30                  35

AAA GGC ACC AGA GAA ATG GTC AAC GCA TGG TTT GCT GAG AGA GTT CAC          257
Lys Gly Thr Arg Glu Met Val Asn Ala Trp Phe Ala Glu Arg Val His
     40                  45                  50

ACC ATT CCT GTG TGC AAG GAA GGA ATC AAG GGC CAC ACG GAA TCC TGC          305
Thr Ile Pro Val Cys Lys Glu Gly Ile Lys Gly His Thr Glu Ser Cys
 55                  60                  65

TCT TGC CCC TTG CAG CCA AGT CCC CGT GCA GAG AGC AGT GTC CCT GGA          353
Ser Cys Pro Leu Gln Pro Ser Pro Arg Ala Glu Ser Ser Val Pro Gly
 70                  75                  80                  85

ACA CCA ACC AGG AAG ATC TCT GCC TCT GAA TTC GAT CGG CCG CTT AGA          401
Thr Pro Thr Arg Lys Ile Ser Ala Ser Glu Phe Asp Arg Pro Leu Arg
                 90                  95                 100

CCC ATC GTT ATC AAG GAT TCT GAG GGA ACT GTG AGC TTC CTC TCT GAC          449
Pro Ile Val Ile Lys Asp Ser Glu Gly Thr Val Ser Phe Leu Ser Asp
            105                 110                 115

TCA GAC AAG AAG GAA CAG ATG CCT CTA ACC TCC CCA CGG TTT GAT AAT          497
Ser Asp Lys Lys Glu Gln Met Pro Leu Thr Ser Pro Arg Phe Asp Asn
        120                 125                 130

GAT GAA GGG GAC CAG TGC TCG AGA CTC TTG GAA TTA GTG AAA GAT ATT          545
Asp Glu Gly Asp Gln Cys Ser Arg Leu Leu Glu Leu Val Lys Asp Ile
    135                 140                 145

TCT AGT CAC TTG GAT GTC ACA GCC TTA TGT CAC AAA ATT TTC TTG CAC          593
Ser Ser His Leu Asp Val Thr Ala Leu Cys His Lys Ile Phe Leu His
150                 155                 160                 165

ATC CAT GGA CTC ATC TCC GCC GAC CGC TAC TCC TTA TTC CTC GTC TGT          641
Ile His Gly Leu Ile Ser Ala Asp Arg Tyr Ser Leu Phe Leu Val Cys
                170                 175                 180

GAG GAC AGC TCC AAC GAC AAG TTT CTT ATC AGC CGC CTC TTT GAT GTT          689
Glu Asp Ser Ser Asn Asp Lys Phe Leu Ile Ser Arg Leu Phe Asp Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 185 |     |     |     |     | 190 |     |     |     |     | 195 |     |     |     |      |
| GCA | GAA | GGT | TCA | ACA | CTG | GAA | GAA | GCT | TCA | AAC | AAC | TGC | ATC | CGC | TTA | 737  |
| Ala | Glu | Gly | Ser | Thr | Leu | Glu | Glu | Ala | Ser | Asn | Asn | Cys | Ile | Arg | Leu |      |
|     |     | 200 |     |     |     | 205 |     |     |     |     | 210 |     |     |     |     |      |
| GAG | TGG | AAC | AAA | GGC | ATC | GTG | GGA | CAC | GTG | GCC | GCT | TTT | GGC | GAG | CCC | 785  |
| Glu | Trp | Asn | Lys | Gly | Ile | Val | Gly | His | Val | Ala | Ala | Phe | Gly | Glu | Pro |      |
|     | 215 |     |     |     | 220 |     |     |     |     | 225 |     |     |     |     |     |      |
| TTG | AAC | ATC | AAA | GAC | GCC | TAT | GAG | GAT | CCT | CGA | TTC | AAT | GCA | GAA | GTT | 833  |
| Leu | Asn | Ile | Lys | Asp | Ala | Tyr | Glu | Asp | Pro | Arg | Phe | Asn | Ala | Glu | Val |      |
| 230 |     |     |     | 235 |     |     |     |     | 240 |     |     |     |     | 245 |     |      |
| GAC | CAA | ATT | ACA | GGC | TAC | AAG | ACA | CAA | AGT | ATT | CTT | TGT | ATG | CCA | ATT | 881  |
| Asp | Gln | Ile | Thr | Gly | Tyr | Lys | Thr | Gln | Ser | Ile | Leu | Cys | Met | Pro | Ile |      |
|     |     |     | 250 |     |     |     |     | 255 |     |     |     |     | 260 |     |     |      |
| AAG | AAT | CAT | AGG | GAA | GAG | GTT | GTT | GGT | GTA | GCC | CAG | GCC | ATC | AAC | AAG | 929  |
| Lys | Asn | His | Arg | Glu | Glu | Val | Val | Gly | Val | Ala | Gln | Ala | Ile | Asn | Lys |      |
|     | 265 |     |     |     |     | 270 |     |     |     |     | 275 |     |     |     |     |      |
| AAA | TCA | GGA | AAT | GGT | GGG | ACA | TTC | ACT | GAA | AAA | GAC | GAA | AAG | GAC | TTT | 977  |
| Lys | Ser | Gly | Asn | Gly | Gly | Thr | Phe | Thr | Glu | Lys | Asp | Glu | Lys | Asp | Phe |      |
|     |     | 280 |     |     |     |     | 285 |     |     |     |     | 290 |     |     |     |      |
| GCT | GCT | TAC | TTG | GCA | TTT | TGT | GGA | ATT | GTT | CTT | CAT | AAT | GCT | CAA | CTC | 1025 |
| Ala | Ala | Tyr | Leu | Ala | Phe | Cys | Gly | Ile | Val | Leu | His | Asn | Ala | Gln | Leu |      |
|     | 295 |     |     |     |     | 300 |     |     |     |     | 305 |     |     |     |     |      |
| TAT | GAG | ACT | TCA | CTG | CTG | GAG | AAC | AAG | AGA | AAT | CAG | GTG | CTG | CTT | GAC | 1073 |
| Tyr | Glu | Thr | Ser | Leu | Leu | Glu | Asn | Lys | Arg | Asn | Gln | Val | Leu | Leu | Asp |      |
| 310 |     |     |     |     | 315 |     |     |     |     | 320 |     |     |     |     | 325 |      |
| CTT | GCT | AGC | TTA | ATT | TTT | GAA | GAA | CAA | CAA | TCA | TTA | GAA | GTA | ATT | CTA | 1121 |
| Leu | Ala | Ser | Leu | Ile | Phe | Glu | Glu | Gln | Gln | Ser | Leu | Glu | Val | Ile | Leu |      |
|     |     |     | 330 |     |     |     |     | 335 |     |     |     |     | 340 |     |     |      |
| AAG | AAA | ATA | GCT | GCC | ACT | ATT | ATC | TCT | TTC | ATG | CAG | GTG | CAG | AAA | TGC | 1169 |
| Lys | Lys | Ile | Ala | Ala | Thr | Ile | Ile | Ser | Phe | Met | Gln | Val | Gln | Lys | Cys |      |
|     |     |     | 345 |     |     |     |     | 350 |     |     |     |     | 355 |     |     |      |
| ACC | ATT | TTC | ATA | GTG | GAT | GAA | GAT | TGC | TCC | GAT | TCT | TTT | TCT | AGT | GTG | 1217 |
| Thr | Ile | Phe | Ile | Val | Asp | Glu | Asp | Cys | Ser | Asp | Ser | Phe | Ser | Ser | Val |      |
|     |     | 360 |     |     |     |     | 365 |     |     |     |     | 370 |     |     |     |      |
| TTT | CAC | ATG | GAG | TGT | GAG | GAA | TTA | GAA | AAA | TCG | TCA | GAT | ACT | TTA | ACA | 1265 |
| Phe | His | Met | Glu | Cys | Glu | Glu | Leu | Glu | Lys | Ser | Ser | Asp | Thr | Leu | Thr |      |
|     | 375 |     |     |     |     | 380 |     |     |     |     | 385 |     |     |     |     |      |
| CGG | GAA | CGT | GAT | GCA | AAC | AGA | ATC | AAT | TAC | ATG | TAT | GCT | CAG | TAT | GTC | 1313 |
| Arg | Glu | Arg | Asp | Ala | Asn | Arg | Ile | Asn | Tyr | Met | Tyr | Ala | Gln | Tyr | Val |      |
| 390 |     |     |     |     | 395 |     |     |     |     | 400 |     |     |     |     | 405 |      |
| AAA | AAT | ACC | ATG | GAA | CCA | CTT | AAT | ATC | CCA | GAC | GTC | AGT | AAG | GAC | AAA | 1361 |
| Lys | Asn | Thr | Met | Glu | Pro | Leu | Asn | Ile | Pro | Asp | Val | Ser | Lys | Asp | Lys |      |
|     |     |     |     | 410 |     |     |     |     | 415 |     |     |     |     | 420 |     |      |
| AGA | TTT | CCC | TGG | ACA | AAT | GAA | AAC | ATG | GGA | AAT | ATA | AAC | CAG | CAG | TGC | 1409 |
| Arg | Phe | Pro | Trp | Thr | Asn | Glu | Asn | Met | Gly | Asn | Ile | Asn | Gln | Gln | Cys |      |
|     |     |     | 425 |     |     |     |     | 430 |     |     |     |     | 435 |     |     |      |
| ATT | AGA | AGT | TTG | CTT | TGT | ACA | CCT | ATA | AAA | AAT | GGA | AAG | AAG | AAC | AAA | 1457 |
| Ile | Arg | Ser | Leu | Leu | Cys | Thr | Pro | Ile | Lys | Asn | Gly | Lys | Lys | Asn | Lys |      |
|     |     |     | 440 |     |     |     |     | 445 |     |     |     |     | 450 |     |     |      |
| GTG | ATA | GGG | GTT | TGC | CAA | CTT | GTT | AAT | AAG | ATG | GAG | GAA | ACC | ACT | GGC | 1505 |
| Val | Ile | Gly | Val | Cys | Gln | Leu | Val | Asn | Lys | Met | Glu | Glu | Thr | Thr | Gly |      |
|     |     | 455 |     |     |     |     | 460 |     |     |     |     | 465 |     |     |     |      |
| AAA | GTT | AAG | GCT | TTC | AAC | CGC | AAC | GAT | GAA | CAG | TTT | CTG | GAA | GCT | TTC | 1553 |
| Lys | Val | Lys | Ala | Phe | Asn | Arg | Asn | Asp | Glu | Gln | Phe | Leu | Glu | Ala | Phe |      |
| 470 |     |     |     | 475 |     |     |     |     | 480 |     |     |     |     | 485 |     |      |
| GTC | ATC | TTT | TGT | GGC | TTG | GGG | ATC | CAG | AAC | ACA | CAG | ATG | TAC | GAA | GCA | 1601 |
| Val | Ile | Phe | Cys | Gly | Leu | Gly | Ile | Gln | Asn | Thr | Gln | Met | Tyr | Glu | Ala |      |
|     |     |     |     | 490 |     |     |     |     | 495 |     |     |     |     | 500 |     |      |
| GTG | GAG | AGA | GCC | ATG | GCC | AAG | CAA | ATG | GTC | ACG | TTA | GAG | GTT | CTG | TCT | 1649 |
| Val | Glu | Arg | Ala | Met | Ala | Lys | Gln | Met | Val | Thr | Leu | Glu | Val | Leu | Ser |      |

-continued

|     | 505 |     |     |     | 510 |     |     |     | 515 |     |     |     |      |
|-----|-----|-----|-----|-----|-----|-----|-----|-----|-----|-----|-----|-----|------|
| TAT | CAT | GCT | TCA | GCT | GCA | GAG | GAA | GAA | ACC | AGA | GAG | CTG | CAG TCC TTA | 1697 |
| Tyr | His | Ala | Ser | Ala | Ala | Glu | Glu | Glu | Thr | Arg | Glu | Leu | Gln Ser Leu |
|     |     | 520 |     |     |     | 525 |     |     |     | 530 |     |     |      |

```
TAT CAT GCT TCA GCT GCA GAG GAA GAA ACC AGA GAG CTG CAG TCC TTA      1697
Tyr His Ala Ser Ala Ala Glu Glu Glu Thr Arg Glu Leu Gln Ser Leu
        520             525             530

GCG GCT GCT GTG GTA CCA TCT GCC CAG ACC CTT AAA ATC ACT GAC TTC      1745
Ala Ala Ala Val Val Pro Ser Ala Gln Thr Leu Lys Ile Thr Asp Phe
        535             540             545

AGC TTC AGC GAC TTT GAG CTG TCT GAC CTG GAA ACA GCA CTG TGC ACA      1793
Ser Phe Ser Asp Phe Glu Leu Ser Asp Leu Glu Thr Ala Leu Cys Thr
550             555             560             565

ATC CGG ATG TTC ACT GAC CTC AAC CTT GTG CAG AAC TTC CAG ATG AAA      1841
Ile Arg Met Phe Thr Asp Leu Asn Leu Val Gln Asn Phe Gln Met Lys
            570             575             580

CAT GAG GTC CTT TGC AAG TGG ATT TTA AGT GTG AAG AAG AAC TAT CGG      1889
His Glu Val Leu Cys Lys Trp Ile Leu Ser Val Lys Lys Asn Tyr Arg
        585             590             595

AAG AAC GTC GCC TAT CAT AAT TGG AGA CAT GCC TTT AAT ACA GCT CAG      1937
Lys Asn Val Ala Tyr His Asn Trp Arg His Ala Phe Asn Thr Ala Gln
            600             605             610

TGC ATG TTT GCG GCA CTA AAA GCA GGC AAA ATT CAG AAG AGG CTG ACG      1985
Cys Met Phe Ala Ala Leu Lys Ala Gly Lys Ile Gln Lys Arg Leu Thr
615             620             625

GAC CTG GAG ATA CTT GCA CTG CTG ATT GCT GCC TTA AGC CAT GAT CTG      2033
Asp Leu Glu Ile Leu Ala Leu Leu Ile Ala Ala Leu Ser His Asp Leu
630             635             640             645

GAT CAC CGT GGT GTC AAT AAC TCA TAC ATA CAG CGA AGT GAA CAC CCA      2081
Asp His Arg Gly Val Asn Asn Ser Tyr Ile Gln Arg Ser Glu His Pro
            650             655             660

CTT GCT CAG CTC TAC TGC CAT TCA ATC ATG GAG CAT CAT CAT TTT GAT      2129
Leu Ala Gln Leu Tyr Cys His Ser Ile Met Glu His His His Phe Asp
        665             670             675

CAG TGC CTG ATG ATC CTT AAT AGT CCT GGC AAT CAG ATT CTC AGT GGC      2177
Gln Cys Leu Met Ile Leu Asn Ser Pro Gly Asn Gln Ile Leu Ser Gly
            680             685             690

CTC TCC ATT GAA GAG TAT AAG ACC ACC CTG AAG ATC ATC AAG CAA GCT      2225
Leu Ser Ile Glu Glu Tyr Lys Thr Thr Leu Lys Ile Ile Lys Gln Ala
        695             700             705

ATT TTA GCC ACA GAC CTA GCA CTG TAC ATA AAG AGA CGA GGA GAA TTT      2273
Ile Leu Ala Thr Asp Leu Ala Leu Tyr Ile Lys Arg Arg Gly Glu Phe
710             715             720             725

TTT GAA CTT ATA ATG AAA AAT CAA TTC AAT TTG GAA GAT CCT CAT CAA      2321
Phe Glu Leu Ile Met Lys Asn Gln Phe Asn Leu Glu Asp Pro His Gln
            730             735             740

AAG GAG TTG TTT TTA GCG ATG CTG ATG ACA GCT TGT GAT CTT TCT GCA      2369
Lys Glu Leu Phe Leu Ala Met Leu Met Thr Ala Cys Asp Leu Ser Ala
        745             750             755

ATT ACA AAA CCC TGG CCT ATT CAA CAA CGG ATA GCA GAA CTT GTT GCC      2417
Ile Thr Lys Pro Trp Pro Ile Gln Gln Arg Ile Ala Glu Leu Val Ala
        760             765             770

ACT GAA TTT TTT GAC CAA GGA GAT AGA GAG AGG AAA GAA CTC AAC ATA      2465
Thr Glu Phe Phe Asp Gln Gly Asp Arg Glu Arg Lys Glu Leu Asn Ile
775             780             785

GAG CCC GCT GAT CTA ATG AAC CGG GAG AAG AAA AAC AAA ATC CCA AGT      2513
Glu Pro Ala Asp Leu Met Asn Arg Glu Lys Lys Asn Lys Ile Pro Ser
        790             795             800             805

ATG CAA GTT GGA TTC ATA GAT GCC ATC TGC TTG CAA CTG TAT GAG GCC      2561
Met Gln Val Gly Phe Ile Asp Ala Ile Cys Leu Gln Leu Tyr Glu Ala
            810             815             820

TTG ACC CAT GTG TCG GAG GAC TGT TTC CCT TTG CTG GAC GGC TGC AGA      2609
Leu Thr His Val Ser Glu Asp Cys Phe Pro Leu Leu Asp Gly Cys Arg
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | 825 |     |     |     | 830 |     |     |     | 835 |     |     |     |     |      |
| AAG | AAC | AGG | CAG | AAA | TGG | CAG | GCT | CTT | GCA | GAA | CAG | CAG | GAG | AAG | ACA  | 2657 |
| Lys | Asn | Arg | Gln | Lys | Trp | Gln | Ala | Leu | Ala | Glu | Gln | Gln | Glu | Lys | Thr  |
|     |     | 840 |     |     |     | 845 |     |     |     | 850 |     |     |     |     |      |
| CTG | ATC | AAT | GGT | GAA | AGC | AGC | CAG | ACC | AAC | CGA | CAG | CAA | CGG | AAT | TCC  | 2705 |
| Leu | Ile | Asn | Gly | Glu | Ser | Ser | Gln | Thr | Asn | Arg | Gln | Gln | Arg | Asn | Ser  |
|     |     | 855 |     |     |     | 860 |     |     |     | 865 |     |     |     |     |      |
| GTT | GCT | GTC | GGG | ACA | GTG | TAGCCAGGTG | TATCAGATGA | GTGAGTGTGT | | | | | | |  2753 |
| Val | Ala | Val | Gly | Thr | Val |
| 870 |     |     |     | 875 |

GCTCAGCTCA GTCCTCTGCA ACACCATGAA GCTAGGCATT CCAGCTTAAT TCCTGCAGTT      2813

GACTTTAAAA AACTGGCATA AAGCACTAGT CAGCATCTAG TTCTAGCTTG ACCAGTGAAG      2873

AGTAGAACAC CACCACAGTC AGGGTGCAGA GCAGTTGGCA GTCTCCTTTC GAACCCAGAC      2933

TGGTGAATTT AAAGAAGAGC AGTCGTCGTT TATATCTCTG TCTTTTCCTA AGCGGGGTGT      2993

GGAATCTCTA AGAGGAGAGA GAGATCTGGA CCACAGGTCC AATGCGCTCT GTCCTCTCAG      3053

CTGCTTCCCC CACTGTGCTG TGACCTCTCA ATCTGAGAAA CGTGTAAGGA AGGTTTCAGC      3113

GAATTCCCTT TAAAATGTGT CAGACAGTAG CTTCTTGGGC CGGGTTGTTC CCGCAGCTCC      3173

CCATCTGTTT GTTGTCTATC TTGGCTGAAA GAGGCTTTGC TGTACCTGCC ACACTCTCCT      3233

GGATCCCTGT CCAGTAGCTG ATCAAAAAAA AGGATGTGAA ATTCTCGTGT GACTTTTTAG      3293

AAAAGGAAAG TGACCCCGAG GATCGGTGTG GATTCACTAG TTGTCCACAG ATGATCTGTT      3353

TAGTTTCTAG AATTTTCCAA GATGATACAC TCCTCCCTAG TCTAGGGGTC AGACCCTGTA      3413

TGGTGGCTGT GACCCTTGAG GAACTTCTCT CTTTGCATGA CATTAGCCAT AGAACTGTTC      3473

TTGTCCAAAT ACACAGCTCA TATGCAGCTT GCAGGAAACA CTTTAAAAAC ACAACTATCA      3533

CCTATGTTAT TCTGATTACA GAAGTTATCC CTACTCACTG TAAACATAAA CAAAGCCCCC      3593

CAAACTTCAA ATAGTTGTGT GTGGTGAGAA ACTGCAAGTT TTCATCTCCA GAGATAGCTA      3653

TAGGTAATAA GTGGGATGTT TCTGAAACTT TTAAAAATAA TCTTTTACAT ATATGTTAAC      3713

TGTTTTCTTA TGAGCACTAT GGTTTGTTTT TTTTTTTTTT TGCTCTGCTT TGACTTGCCC      3773

TTTTCACTCA ATTATCTTGG CAGTTTTTCT AAATGACTTG CACAGACTTC TCCTGTACTT      3833

CATGGCTGTG CAGTGTTCCA TGCTGTGAGG GCACCATCGT GTATTAAATC AGTTCCCTGG      3893

TCACACATAG GTGAGCTGGT TGGAAATTTT TACCATTAAA AAACCACTTT CCCACATTGA      3953

TGCTTTCTAA TCTGGCACAG GATGCTTCTT TTTTTCCCCT TTTTCTCTGT TTAATTATTG      4013

GAAATGGGAT CTGTGGGATC CTCGTTCCCT GGCACCTAGC TGCTCTCAAC GTGGCCTGTG      4073

GCCAGCAGCA TTGGCTAGAC CTGGGGGCTT GTTGGGAACG GAGACCCTCT GCCCTGCCCC      4133

TGGCCTGCTG ACAAGGACCT GCATTTTGCT GAGCTCCCAG TGACCCTGGT GTTTAATTGT      4193

TAACCATTGA AAAAAATCAA ACTATAGTTT ATTTACAATG TTGTGTTAAT TTCGGGTGTA      4253

CAGCAAAGTG ACTCAGTGGT CAAGTACATT TAAAACACTG GCATACTCT CTCCCTCTCC       4313

TTGTGTACCT GGTTGGTATT TCCAGAAACC ATGCTCTTGT CTGTCCTGTA GTTTTGGAAG      4373

CGCTTTCTCT TTGAAGACTG CCTTCTCTCC TCTGTCTGCC CTACATGGAC TAGTTCGTTT      4433

ATTGTCCTAC ATGGCTTTGC TTCCATGTTC CTCTCAACTT T                         4474

(2) INFORMATION FOR SEQ ID NO:10:

(i) SEQUENCE CHARACTERISTICS:
       (A) LENGTH: 875 amino acids
       (B) TYPE: amino acid
       (D) TOPOLOGY: linear (ii) MOLECULE TYPE: protein (xi) SEQUENCE DESCRIPTION: SEQ ID NO:10:

```
Met Glu Arg Ala Gly Pro Gly Ser Ala Arg Pro Gln Gln Gln Trp Asp
 1               5                  10                  15

Gln Asp Ser Val Glu Ala Trp Leu Asp Asp His Trp Asp Phe Thr Phe
                20                  25                  30

Ser Tyr Phe Val Arg Lys Gly Thr Arg Glu Met Val Asn Ala Trp Phe
            35                  40                  45

Ala Glu Arg Val His Thr Ile Pro Val Cys Lys Glu Gly Ile Lys Gly
        50                  55                  60

His Thr Glu Ser Cys Ser Cys Pro Leu Gln Pro Ser Pro Arg Ala Glu
 65                 70                  75                  80

Ser Ser Val Pro Gly Thr Pro Thr Arg Lys Ile Ser Ala Ser Glu Phe
                85                  90                  95

Asp Arg Pro Leu Arg Pro Ile Val Ile Lys Asp Ser Glu Gly Thr Val
            100                 105                 110

Ser Phe Leu Ser Asp Ser Asp Lys Lys Glu Gln Met Pro Leu Thr Ser
        115                 120                 125

Pro Arg Phe Asp Asn Asp Glu Gly Asp Gln Cys Ser Arg Leu Leu Glu
    130                 135                 140

Leu Val Lys Asp Ile Ser His Leu Asp Val Thr Ala Leu Cys His
145                 150                 155                 160

Lys Ile Phe Leu His Ile His Gly Leu Ile Ser Ala Asp Arg Tyr Ser
                165                 170                 175

Leu Phe Leu Val Cys Glu Asp Ser Ser Asn Asp Lys Phe Leu Ile Ser
            180                 185                 190

Arg Leu Phe Asp Val Ala Glu Gly Ser Thr Leu Glu Glu Ala Ser Asn
        195                 200                 205

Asn Cys Ile Arg Leu Glu Trp Asn Lys Gly Ile Val Gly His Val Ala
    210                 215                 220

Ala Phe Gly Glu Pro Leu Asn Ile Lys Asp Ala Tyr Glu Asp Pro Arg
225                 230                 235                 240

Phe Asn Ala Glu Val Asp Gln Ile Thr Gly Tyr Lys Thr Gln Ser Ile
                245                 250                 255

Leu Cys Met Pro Ile Lys Asn His Arg Glu Val Val Gly Val Ala
            260                 265                 270

Gln Ala Ile Asn Lys Lys Ser Gly Asn Gly Gly Thr Phe Thr Glu Lys
        275                 280                 285

Asp Glu Lys Asp Phe Ala Ala Tyr Leu Ala Phe Cys Gly Ile Val Leu
    290                 295                 300

His Asn Ala Gln Leu Tyr Glu Thr Ser Leu Leu Glu Asn Lys Arg Asn
305                 310                 315                 320

Gln Val Leu Leu Asp Leu Ala Ser Leu Ile Phe Glu Glu Gln Gln Ser
                325                 330                 335

Leu Glu Val Ile Leu Lys Lys Ile Ala Ala Thr Ile Ile Ser Phe Met
            340                 345                 350

Gln Val Gln Lys Cys Thr Ile Phe Ile Val Asp Glu Asp Cys Ser Asp
        355                 360                 365

Ser Phe Ser Ser Val Phe His Met Glu Cys Glu Glu Leu Glu Lys Ser
    370                 375                 380

Ser Asp Thr Leu Thr Arg Glu Arg Asp Ala Asn Arg Ile Asn Tyr Met
385                 390                 395                 400

Tyr Ala Gln Tyr Val Lys Asn Thr Met Glu Pro Leu Asn Ile Pro Asp
```

-continued

```
                405                 410                 415
Val Ser Lys Asp Lys Arg Phe Pro Trp Thr Asn Glu Asn Met Gly Asn
            420                 425                 430
Ile Asn Gln Gln Cys Ile Arg Ser Leu Leu Cys Thr Pro Ile Lys Asn
            435                 440                 445
Gly Lys Lys Asn Lys Val Ile Gly Val Cys Gln Leu Val Asn Lys Met
            450                 455                 460
Glu Glu Thr Thr Gly Lys Val Lys Ala Phe Asn Arg Asn Asp Glu Gln
465                 470                 475                 480
Phe Leu Glu Ala Phe Val Ile Phe Cys Gly Leu Gly Ile Gln Asn Thr
                485                 490                 495
Gln Met Tyr Glu Ala Val Glu Arg Ala Met Ala Lys Gln Met Val Thr
            500                 505                 510
Leu Glu Val Leu Ser Tyr His Ala Ser Ala Ala Glu Glu Thr Arg
            515                 520                 525
Glu Leu Gln Ser Leu Ala Ala Ala Val Val Pro Ser Ala Gln Thr Leu
            530                 535                 540
Lys Ile Thr Asp Phe Ser Phe Ser Asp Phe Glu Leu Ser Asp Leu Glu
545                 550                 555                 560
Thr Ala Leu Cys Thr Ile Arg Met Phe Thr Asp Leu Asn Leu Val Gln
                565                 570                 575
Asn Phe Gln Met Lys His Glu Val Leu Cys Lys Trp Ile Leu Ser Val
            580                 585                 590
Lys Lys Asn Tyr Arg Lys Asn Val Ala Tyr His Asn Trp Arg His Ala
            595                 600                 605
Phe Asn Thr Ala Gln Cys Met Phe Ala Ala Leu Lys Ala Gly Lys Ile
            610                 615                 620
Gln Lys Arg Leu Thr Asp Leu Glu Ile Leu Ala Leu Leu Ile Ala Ala
625                 630                 635                 640
Leu Ser His Asp Leu Asp His Arg Gly Val Asn Asn Ser Tyr Ile Gln
                645                 650                 655
Arg Ser Glu His Pro Leu Ala Gln Leu Tyr Cys His Ser Ile Met Glu
            660                 665                 670
His His His Phe Asp Gln Cys Leu Met Ile Leu Asn Ser Pro Gly Asn
            675                 680                 685
Gln Ile Leu Ser Gly Leu Ser Ile Glu Glu Tyr Lys Thr Thr Leu Lys
            690                 695                 700
Ile Ile Lys Gln Ala Ile Leu Ala Thr Asp Leu Ala Leu Tyr Ile Lys
705                 710                 715                 720
Arg Arg Gly Glu Phe Phe Glu Leu Ile Met Lys Asn Gln Phe Asn Leu
                725                 730                 735
Glu Asp Pro His Gln Lys Glu Leu Phe Leu Ala Met Leu Met Thr Ala
            740                 745                 750
Cys Asp Leu Ser Ala Ile Thr Lys Pro Trp Pro Ile Gln Gln Arg Ile
            755                 760                 765
Ala Glu Leu Val Ala Thr Glu Phe Phe Asp Gln Gly Asp Arg Glu Arg
            770                 775                 780
Lys Glu Leu Asn Ile Glu Pro Ala Asp Leu Met Asn Arg Glu Lys Lys
785                 790                 795                 800
Asn Lys Ile Pro Ser Met Gln Val Gly Phe Ile Asp Ala Ile Cys Leu
                805                 810                 815
Gln Leu Tyr Glu Ala Leu Thr His Val Ser Glu Asp Cys Phe Pro Leu
            820                 825                 830
```

```
Leu Asp Gly Cys Arg Lys Asn Arg Gln Lys Trp Gln Ala Leu Ala Glu
            835                 840                 845

Gln Gln Glu Lys Thr Leu Ile Asn Gly Glu Ser Ser Gln Thr Asn Arg
    850                 855                 860

Gln Gln Arg Asn Ser Val Ala Val Gly Thr Val
865                 870                 875
```

(2) INFORMATION FOR SEQ ID NO:11:

(i) SEQUENCE CHARACTERISTICS:
        (A) LENGTH: 2060 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GCGGCCGCGC TCCGGCCGCT TTGTCGAAAG CCGGCCCGAC TGGAGCAGGA CGAAGGGGGA    60

GGGTCTCGAG GCCGAGTCCT GTTCTTCTGA GGGACGGACC CCAGCTGGGG TGGAAAAGCA   120

GTACCAGAGA GCCTCCGAGG CGCGCGGTGC CAACCATGGA GCGGGCCGGC CCCAGCTTCG   180

GGCAGCAGCG ACAGCAGCAG CAGCCCCAGC AGCAGAAGCA GCAGCAGAGG GATCAGGACT   240

CGGTCGAAGC ATGGCTGGAC GATCACTGGG ACTTTACCTT CTCATACTTT GTTAGAAAAG   300

CCACCAGAGA AATGGTCAAT GCATGGTTTG CTGAGAGAGT TCACACCATC CCTGTGTGCA   360

AGGAAGGTAT CAGAGGCCAC ACCGAATCTT GCTCTTGTCC CTTGCAGCAG AGTCCTCGTG   420

CAGATAACAG TGTCCCTGGA ACACCAACCA GGAAAATCTC TGCCTCTGAA TTTGACCGGC   480

CTCTTAGACC CATTGTTGTC AAGGATTCTG AGGGAACTGT GAGCTTCCTC TCTGACTCAG   540

AAAAGAAGGA ACAGATGCCT CTAACCCCTC AAGGTTTGA TCATGATGAA GGGGACCAGT   600

GCTCAAGACT CTTGGAATTA GTGAAGGATA TTTCTAGTCA TTTGGATGTC ACAGCCTTAT   660

GTCACAAAAT TTTCTTGCAT ATCCATGGAC TGATATCTGC TGACCGCTAT TCCCTGTTCC   720

TTGTCTGTGA AGACAGCTCC AATGACAAGT TTCTTATCAG CCGCCTCTTT GATGTTGCTG   780

AAGGTTCAAC ACTGGAAGAA GTTTCAAATA ACTGTATCCG CTTAGAATGG AACAAAGGCA   840

TTGTGGGACA TGTGGCAGCG CTTGGTGAGC CCTTGAACAT CAAAGATGCA TATGAGGATC   900

CTCGGTTCAA TGCAGAAGTT GACCAAATTA CAGGCTACAA GACACAAAGC ATTCTTTGTA   960

TGCCAATTAA GAATCATAGG GAAGAGGTTG TTGGTGTAGC CCAGGCCATC AACAAGAAAT  1020

CAGGAAACGG TGGGACATTT ACTGAAAAAG ATGAAAAGGA CTTTGCTGCT TATTTGGCAT  1080

TTTGTGGTAT TGTTCTTCAT AATGCTCAGC TCTATGAGAC TTCACTGCTG GAGAACAAGA  1140

GAAATCAGGT GCTGCTTGAC CTTGCTAGTT TAATTTTTGA AGAACAACAA TCATTAGAAG  1200

TAATTTTGAA GAAAATAGCT GCCACTATTA TCTCTTTCAT GCAAGTGCAG AAATGCACCA  1260

TTTTCATAGT GGATGAAGAT TGCTCCGATT CTTTTTCTAG TGTGTTTCAC ATGGAGTGTG  1320

AGGAATTAGA AAAATCATCT GATACATTAA CAAGGGAACA TGATGCAAAC AAAATCAATT  1380

ACATGTATGC TCAGTATGTC AAAAATACTA TGGAACCACT TTATATCCCA GATGTCAGTA  1440

AGGATAAAAG ATTTCCCTGG ACAACTGAAA ATACAGGAAA TGTAACCAG CAGTGCATTA  1500

GAAGTTTGCT TTGTACACCT ATAAAAAATG GAAAGAAGAA TAAAGTTATA GGGGTTTGCC  1560

AACTTGTTAA TAAGATGGAG GAGAATACTG GCAAGGTTAA GCCTTTCAAC CGAAATGACG  1620

AACAGTTTCT GGAAGCTTTT GTCATCTTTT GTGGCTTGGG GATCCAGAAC ACGCAGATGT  1680

ATGAAGCAGT GGAGAGAGCC ATGGCCAAGC AAATGGTCAC ATTGGAGGTT CTGTCGTATC  1740
```

```
ATGCTTCAGC AGCAGAGGAA GAAACAAGAG AGCTACAGTC GTTAGCGGCT GCTGTGGTGC      1800

CATCTGCCCA GACCCTTAAA ATTACTGACT TTAGCTTCAG TGACTTTGAG CTGTCTGATC      1860

TGGAAACAGC ACTGTGTACA ATTCGGATGT TTACTGACCT CAACCTTGTG CAGAACTTCC      1920

AGATGAAACA TGAGGTTCTT TGCAGATGGA TTTTAAGTGT TAAGAAGAAT TATCGGAAGA      1980

ATGTTGCCTA TCATAATTGG AGACATGCCT TTAATACAGC TCAGTGCATG TTTGCTGCTC      2040

TAAAAGCAGG CAAAATTCAG                                                  2060

(2) INFORMATION FOR SEQ ID NO:12:

(i) SEQUENCE CHARACTERISTICS:
        (A) LENGTH: 1982 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ACAAAATTTT CTTGCATATC CATGGACTGA TATCTGCTGA CCGCTATTCC CTGTTCCTTG        60

TCTGTGAAGA CAGCTCCAAT GACAAGTTTC TTATCAGCCG CCTCTTTGAT GTTGCTGAAG       120

GTTCAACACT GGAAGAAGTT TCAAATAACT GTATCCGCTT AGAATGGAAC AAAGGCATTG       180

TGGGACATGT GGCAGCGCTT GGTGAGCCCT TGAACATCAA AGATGCATAT GAGGATCCTC       240

GGTTCAATGC AGAAGTTGAC CAAATTCAG GCTACAAGAC ACAAAGCATT CTTTGTATGC        300

CAATTAAGAA TCATAGGGAA GAGGTTGTTG GTGTAGCCCA GGCCATCAAC AAGAAATCAG       360

GAAACGGTGG GACATTTACT GAAAAAGATG AAAAGGACTT TGCTGCTTAT TTGGCATTTT       420

GTGGTATTGT TCTTCATAAT GCTCAGCTCT ATGAGACTTC ACTGCTGGAG AACAAGAGAA       480

ATCAGGTGCT GCTTGACCTT GCTAGTTTAA TTTTTGAAGA ACAACAATCA TTAGAAGTAA       540

TTTTGAAGAA AATAGCTGCC ACTATTATCT CTTTCATGCA AGTGCAGAAA TGCACCATTT       600

TCATAGTGGA TGAAGATTGC TCCGATTCTT TTTCTAGTGT GTTTCACATG GAGTGTGAGG       660

AATTAGAAAA ATCATCTGAT ACATTAACAA GGGAACATGA TGCAAACAAA ATCAATTACA       720

TGTATGCTCA GTATGTCAAA AATACTATGG AACCACTTAA TATCCCAGAT GTCAGTAAGG       780

ATAAAAGATT TCCCTGGACA ACTGAAAATA CAGGAAATGT AAACCAGCAG TGCATTAGAA       840

GTTTGCTTTG TACACCTATA AAAAATGGAA AGAAGAATAA AGTTATAGGG GTTTGCCAAC       900

TTGTTAATAA GATGGAGGAG AATACTGGCA AGGTTAAGCC TTTCAACCGA AATGACGAAC       960

AGTTTCTGGA AGCTTTTGTC ATCTTTTGTG GCTTGGGGAT CCAGAACACG CAGATGTATG      1020

AAGCAGTGGA GAGAGCCATG GCCAAGCAAA TGGTCACATT GGAGGTTCTG TCGTATCATG      1080

CTTCAGCAGC AGAGGAAGAA ACAAGAGAGC TACAGTCGTT AGCGGCTGCT GTGGTGCCAT      1140

CTGCCCAGAC CCTTAAAATT ACTGACTTTA GCTTCAGTGA CTTTGAGCTG TCTGATCTGG      1200

AAACAGCACT GTGTACAATT CGGATGTTTA CTGACCTCAA CCTTGTGCAG AACTTCCAGA      1260

TGAAACATGA GGTTCTTTGC AGATGGATTT AAGTGTTAA GAAGAATTAT CGGAAGAATG       1320

TTGCCTATCA TAATTGGAGA CATGCCTTTA ATACAGCTCA GTGCATGTTT GCTGCTCTAA      1380

AAGCAGGCAA AATTCAGAAC AAGCTGACTG ACCTGGAGAT ACTTGCATTG CTGATTGCTG      1440

CACTAAGCCA CGATTTGGAT CACCGTGGTG TGAATAACTC TTACATACAG CGAAGTGAAC      1500

ATCCACTTGC CCAGCTTTAC TGCCATTCAA TCATGGAACA CCATCATTTT GACCAGTGCC      1560

TGATGATTCT TAATAGTCCA GGCAATCAGA TTCTCAGTGG CCTCTCCATT GAAGAATATA      1620

AGACCACGTT GAAAATAATC AAGCAAGCTA TTTTAGCTAC AGACCTAGCA CTGTACATTA      1680
```

```
AGAGGCGAGG AGAATTTTTT GAACTTATAA GAAAAAATCA ATTCAATTTG GAAGATCCTC      1740

ATCAAAAGGA GTTGTTTTTG GCAATGCTGA TGACAGCTTG TGATCTTTCT GCAATTACAA      1800

AACCCTGGCC TATTCAACAA CGGATAGCAG AACTTGTAGC AACTGAATTT TTTGATCAAG      1860

GAGACAGAGA GAGAAAAGAA CTCAACATAG AACCCACTGA TCTAATGAAC AGGGAGAAGA      1920

AAAACAAAAT CCCAAGTATG CAAGTTGGGT TCATAGATGC CATCTGCTTG CAACTGTATG      1980

AG                                                                    1982

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GCCACCAGAG AAATGGTC                                                      18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ACAATGGGTC TAAGAGGC                                                      18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TCAGTGCATG TTTGCTGC                                                      18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TACAAACATG TTCATCAG                                                      18

(2) INFORMATION FOR SEQ ID NO:17:

(i) SEQUENCE CHARACTERISTICS:
        (A) LENGTH: 1107 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO:17:

```
GAGACATGCC TTTAATACAG CTCAGTGCAT GTTTGCTGCT CTAAAAGCAG GCAAAATTCA        60
GAACAAGCTG ACTGACCTGG AGATACTTGC ATTGCTGATT GCTGCACTAA GCCACGATTT       120
GGATCACCGT GGTGTGAATA ACTCTTACAT ACAGCGAAGT GAACATCCAC TTGCCCAGCT       180
TTACTGCCAT TCAATCATGG AACACCATCA TTTTGACCAG TGCCTGATGA TTCTTAATAG       240
TCCAGGCAAT CAGATTCTCA GTGGCCTCTC CATTGAAGAA TATAAGACCA CGTTGAAAAT       300
AATCAAGCAA GCTATTTTAG CTACAGACCT AGCACTGTAC ATTAAGAGGC GAGGAGAATT       360
TTTTGAACTT ATAAGAAAAA ATCAATTCAA TTTGGAAGAT CCTCATCAAA AGGAGTTGTT       420
TTTGGCAATG CTGATGACAG CTTGTGATCT TTCTGCAATT ACAAAACCCT GGCCTATTCA       480
ACAACGGATA GCAGAACTTG TAGCAACTGA ATTTTTTGAT CAAGGAGACA GAGAGAGAAA       540
AGAACTCAAC ATAGAACCCA CTGATCTAAT GAACAGGGAG AAGAAAAACA AAATCCCAAG       600
TATGCAAGTT GGGTTCATAG ATGCCATCTG CTTGCAACTG TATGAGGCCC TGACCCACGT       660
GTCAGAGGAC TGTTTCCCTT TGCTAGATGG CTGCAGAAAG AACAGGCAGA ATGGCAGGC       720
CCTTGCAGAA CAGCAGGAGA AGATGCTGAT TAATGGGGAA AGCGGCCAGG CCAAGCGGAA       780
CTGAGTGGCC TATTTCATGC AGAGTTGAAG TTTACAGAGA TGGTGTGTTC TGCAATATGC       840
CTAGTTTCTT ACACACTGTC TGTATAGTGT CTGTATTTGG TATATACTTT GCCACTGCTG       900
TATTTTTATT TTTGCACAAC TTTTGAGAGT ATAGCATGAA TGTTTTTAGA GGACTATTAC       960
ATATTTTTTG TATATTTGTT TTATGCTACT GAACTGAAAG GATCAACAAC ATCCACTGTT      1020
AGCACATTGA TAAAAGCATT GTTTGTGATA TTTCGTGTAC TGCAAAGTGT ATGCAGTATT      1080
CTTGCACTGA GGTTTTTTTG CTTGGGG                                         1107
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
TTTGGAAGAT CCTCATCA                                                      18
```

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
ATGTCTCGAG TCAGTTCCGC TTGGCCTG                                           28
```

(2) INFORMATION FOR SEQ ID NO:20:

(i) SEQUENCE CHARACTERISTICS:
        (A) LENGTH: 30 base pairs
        (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:20:

TACAGAATTC TGACCATGGA GCGGGCCGGC                                          30

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

CATTCTAAGC GGATACAG                                                      18

(2) INFORMATION FOR SEQ ID NO:22:

(i) SEQUENCE CHARACTERISTICS:
            (A) LENGTH: 2645 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 12..2636

(xi) SEQUENCE DESCRIPTION: SEQ ID NO:22:
```

```
GAATTCTGAC C ATG GAG CGG GCC GGC CCC AGC TTC GGG CAG CAG CGA CAG        50
             Met Glu Arg Ala Gly Pro Ser Phe Gly Gln Gln Arg Gln
              1               5                  10

CAG CAG CAG CCC CAG CAG CAG AAG CAG CAG CAG AGG GAT CAG GAC TCG        98
Gln Gln Gln Pro Gln Gln Gln Lys Gln Gln Gln Arg Asp Gln Asp Ser
         15                  20                  25

GTC GAA GCA TGG CTG GAC GAT CAC TGG GAC TTT ACC TTC TCA TAC TTT       146
Val Glu Ala Trp Leu Asp Asp His Trp Asp Phe Thr Phe Ser Tyr Phe
 30                  35                  40                  45

GTT AGA AAA GCC ACC AGA GAA ATG GTC AAT GCA TGG TTT GCT GAG AGA       194
Val Arg Lys Ala Thr Arg Glu Met Val Asn Ala Trp Phe Ala Glu Arg
                 50                  55                  60

GTT CAC ACC ATC CCT GTG TGC AAG GAA GGT ATC AGA GGC CAC ACC GAA       242
Val His Thr Ile Pro Val Cys Lys Glu Gly Ile Arg Gly His Thr Glu
             65                  70                  75

TCT TGC TCT TGT CCC TTG CAG CAG AGT CCT CGT GCA GAT AAC AGT GTC       290
Ser Cys Ser Cys Pro Leu Gln Gln Ser Pro Arg Ala Asp Asn Ser Val
         80                  85                  90

CCT GGA ACA CCA ACC AGG AAA ATC TCT GCC TCT GAA TTT GAC CGG CCT       338
Pro Gly Thr Pro Thr Arg Lys Ile Ser Ala Ser Glu Phe Asp Arg Pro
     95                  100                 105

CTT AGA CCC ATT GTT GTC AAG GAT TCT GAG GGA ACT GTG AGC TTC CTC       386
Leu Arg Pro Ile Val Val Lys Asp Ser Glu Gly Thr Val Ser Phe Leu
110                 115                 120                 125

TCT GAC TCA GAA AAG AAG GAA CAG ATG CCT CTA ACC CCT CCA AGG TTT       434
Ser Asp Ser Glu Lys Lys Glu Gln Met Pro Leu Thr Pro Pro Arg Phe
                 130                 135                 140

GAT CAT GAT GAA GGG GAC CAG TGC TCA AGA CTC TTG GAA TTA GTG AAG       482
Asp His Asp Glu Gly Asp Gln Cys Ser Arg Leu Leu Glu Leu Val Lys
             145                 150                 155
```

```
GAT ATT TCT AGT CAT TTG GAT GTC ACA GCC TTA TGT CAC AAA ATT TTC      530
Asp Ile Ser Ser His Leu Asp Val Thr Ala Leu Cys His Lys Ile Phe
        160                 165                 170

TTG CAT ATC CAT GGA CTG ATA TCT GCT GAC CGC TAT TCC CTG TTC CTT      578
Leu His Ile His Gly Leu Ile Ser Ala Asp Arg Tyr Ser Leu Phe Leu
    175                 180                 185

GTC TGT GAA GAC AGC TCC AAT GAC AAG TTT CTT ATC AGC CGC CTC TTT      626
Val Cys Glu Asp Ser Ser Asn Asp Lys Phe Leu Ile Ser Arg Leu Phe
190                 195                 200                 205

GAT GTT GCT GAA GGT TCA ACA CTG GAA GAA GTT TCA AAT AAC TGT ATC      674
Asp Val Ala Glu Gly Ser Thr Leu Glu Glu Val Ser Asn Asn Cys Ile
            210                 215                 220

CGC TTA GAA TGG AAC AAA GGC ATT GTG GGA CAT GTG GCA GCG CTT GGT      722
Arg Leu Glu Trp Asn Lys Gly Ile Val Gly His Val Ala Ala Leu Gly
            225                 230                 235

GAG CCC TTG AAC ATC AAA GAT GCA TAT GAG GAT CCT CGG TTC AAT GCA      770
Glu Pro Leu Asn Ile Lys Asp Ala Tyr Glu Asp Pro Arg Phe Asn Ala
            240                 245                 250

GAA GTT GAC CAA ATT ACA GGC TAC AAG ACA CAA AGC ATT CTT TGT ATG      818
Glu Val Asp Gln Ile Thr Gly Tyr Lys Thr Gln Ser Ile Leu Cys Met
        255                 260                 265

CCA ATT AAG AAT CAT AGG GAA GAG GTT GTT GGT GTA GCC CAG GCC ATC      866
Pro Ile Lys Asn His Arg Glu Glu Val Val Gly Val Ala Gln Ala Ile
270                 275                 280                 285

AAC AAG AAA TCA GGA AAC GGT GGG ACA TTT ACT GAA AAA GAT GAA AAG      914
Asn Lys Lys Ser Gly Asn Gly Gly Thr Phe Thr Glu Lys Asp Glu Lys
                290                 295                 300

GAC TTT GCT GCT TAT TTG GCA TTT TGT GGT ATT GTT CTT CAT AAT GCT      962
Asp Phe Ala Ala Tyr Leu Ala Phe Cys Gly Ile Val Leu His Asn Ala
            305                 310                 315

CAG CTC TAT GAG ACT TCA CTG CTG GAG AAC AAG AGA AAT CAG GTG CTG     1010
Gln Leu Tyr Glu Thr Ser Leu Leu Glu Asn Lys Arg Asn Gln Val Leu
        320                 325                 330

CTT GAC CTT GCT AGT TTA ATT TTT GAA GAA CAA CAA TCA TTA GAA GTA     1058
Leu Asp Leu Ala Ser Leu Ile Phe Glu Glu Gln Gln Ser Leu Glu Val
        335                 340                 345

ATT TTG AAG AAA ATA GCT GCC ACT ATT ATC TCT TTC ATG CAA GTG CAG     1106
Ile Leu Lys Lys Ile Ala Ala Thr Ile Ile Ser Phe Met Gln Val Gln
350                 355                 360                 365

AAA TGC ACC ATT TTC ATA GTG GAT GAA GAT TGC TCC GAT TCT TTT TCT     1154
Lys Cys Thr Ile Phe Ile Val Asp Glu Asp Cys Ser Asp Ser Phe Ser
                370                 375                 380

AGT GTG TTT CAC ATG GAG TGT GAG GAA TTA GAA AAA TCA TCT GAT ACA     1202
Ser Val Phe His Met Glu Cys Glu Glu Leu Glu Lys Ser Ser Asp Thr
            385                 390                 395

TTA ACA AGG GAA CAT GAT GCA AAC AAA ATC AAT TAC ATG TAT GCT CAG     1250
Leu Thr Arg Glu His Asp Ala Asn Lys Ile Asn Tyr Met Tyr Ala Gln
        400                 405                 410

TAT GTC AAA AAT ACT ATG GAA CCA CTT AAT ATC CCA GAT GTC AGT AAG     1298
Tyr Val Lys Asn Thr Met Glu Pro Leu Asn Ile Pro Asp Val Ser Lys
        415                 420                 425

GAT AAA AGA TTT CCC TGG ACA ACT GAA AAT ACA GGA AAT GTA AAC CAG     1346
Asp Lys Arg Phe Pro Trp Thr Thr Glu Asn Thr Gly Asn Val Asn Gln
430                 435                 440                 445

CAG TGC ATT AGA AGT TTG CTT TGT ACA CCT ATA AAA AAT GGA AAG AAG     1394
Gln Cys Ile Arg Ser Leu Leu Cys Thr Pro Ile Lys Asn Gly Lys Lys
                450                 455                 460

AAT AAA GTT ATA GGG GTT TGC CAA CTT GTT AAT AAG ATG GAG GAG AAT     1442
Asn Lys Val Ile Gly Val Cys Gln Leu Val Asn Lys Met Glu Glu Asn
            465                 470                 475
```

```
ACT GGC AAG GTT AAG CCT TTC AAC CGA AAT GAC GAA CAG TTT CTG GAA      1490
Thr Gly Lys Val Lys Pro Phe Asn Arg Asn Asp Glu Gln Phe Leu Glu
        480                 485                 490

GCT TTT GTC ATC TTT TGT GGC TTG GGG ATC CAG AAC ACG CAG ATG TAT      1538
Ala Phe Val Ile Phe Cys Gly Leu Gly Ile Gln Asn Thr Gln Met Tyr
495                 500                 505

GAA GCA GTG GAG AGA GCC ATG GCC AAG CAA ATG GTC ACA TTG GAG GTT      1586
Glu Ala Val Glu Arg Ala Met Ala Lys Gln Met Val Thr Leu Glu Val
510                 515                 520                 525

CTG TCG TAT CAT GCT TCA GCA GCA GAG GAA GAA ACA AGA GAG CTA CAG      1634
Leu Ser Tyr His Ala Ser Ala Ala Glu Glu Glu Thr Arg Glu Leu Gln
                530                 535                 540

TCG TTA GCG GCT GCT GTG GTG CCA TCT GCC CAG ACC CTT AAA ATT ACT      1682
Ser Leu Ala Ala Ala Val Val Pro Ser Ala Gln Thr Leu Lys Ile Thr
            545                 550                 555

GAC TTT AGC TTC AGT GAC TTT GAG CTG TCT GAT CTG GAA ACA GCA CTG      1730
Asp Phe Ser Phe Ser Asp Phe Glu Leu Ser Asp Leu Glu Thr Ala Leu
        560                 565                 570

TGT ACA ATT CGG ATG TTT ACT GAC CTC AAC CTT GTG CAG AAC TTC CAG      1778
Cys Thr Ile Arg Met Phe Thr Asp Leu Asn Leu Val Gln Asn Phe Gln
    575                 580                 585

ATG AAA CAT GAG GTT CTT TGC AGA TGG ATT TTA AGT GTT AAG AAG AAT      1826
Met Lys His Glu Val Leu Cys Arg Trp Ile Leu Ser Val Lys Lys Asn
590                 595                 600                 605

TAT CGG AAG AAT GTT GCC TAT CAT AAT TGG AGA CAT GCC TTT AAT ACA      1874
Tyr Arg Lys Asn Val Ala Tyr His Asn Trp Arg His Ala Phe Asn Thr
                610                 615                 620

GCT CAG TGC ATG TTT GCT GCT CTA AAA GCA GGC AAA ATT CAG AAC AAG      1922
Ala Gln Cys Met Phe Ala Ala Leu Lys Ala Gly Lys Ile Gln Asn Lys
            625                 630                 635

CTG ACT GAC CTG GAG ATA CTT GCA TTG CTG ATT GCT GCA CTA AGC CAC      1970
Leu Thr Asp Leu Glu Ile Leu Ala Leu Leu Ile Ala Ala Leu Ser His
        640                 645                 650

GAT TTG GAT CAC CGT GGT GTG AAT AAC TCT TAC ATA CAG CGA AGT GAA      2018
Asp Leu Asp His Arg Gly Val Asn Asn Ser Tyr Ile Gln Arg Ser Glu
    655                 660                 665

CAT CCA CTT GCC CAG CTT TAC TGC CAT TCA ATC ATG GAA CAC CAT CAT      2066
His Pro Leu Ala Gln Leu Tyr Cys His Ser Ile Met Glu His His His
670                 675                 680                 685

TTT GAC CAG TGC CTG ATG ATT CTT AAT AGT CCA GGC AAT CAG ATT CTC      2114
Phe Asp Gln Cys Leu Met Ile Leu Asn Ser Pro Gly Asn Gln Ile Leu
                690                 695                 700

AGT GGC CTC TCC ATT GAA GAA TAT AAG ACC ACG TTG AAA ATA ATC AAG      2162
Ser Gly Leu Ser Ile Glu Glu Tyr Lys Thr Thr Leu Lys Ile Ile Lys
            705                 710                 715

CAA GCT ATT TTA GCT ACA GAC CTA GCA CTG TAC ATT AAG AGG CGA GGA      2210
Gln Ala Ile Leu Ala Thr Asp Leu Ala Leu Tyr Ile Lys Arg Arg Gly
        720                 725                 730

GAA TTT TTT GAA CTT ATA AGA AAA AAT CAA TTC AAT TTG GAA GAT CCT      2258
Glu Phe Phe Glu Leu Ile Arg Lys Asn Gln Phe Asn Leu Glu Asp Pro
    735                 740                 745

CAT CAA AAG GAG TTG TTT TTG GCA ATG CTG ATG ACA GCT TGT GAT CTT      2306
His Gln Lys Glu Leu Phe Leu Ala Met Leu Met Thr Ala Cys Asp Leu
750                 755                 760                 765

TCT GCA ATT ACA AAA CCC TGG CCT ATT CAA CAA CGG ATA GCA GAA CTT      2354
Ser Ala Ile Thr Lys Pro Trp Pro Ile Gln Gln Arg Ile Ala Glu Leu
                770                 775                 780

GTA GCA ACT GAA TTT TTT GAT CAA GGA GAC AGA GAG AGA AAA GAA CTC      2402
Val Ala Thr Glu Phe Phe Asp Gln Gly Asp Arg Glu Arg Lys Glu Leu
            785                 790                 795
```

```
AAC ATA GAA CCC ACT GAT CTA ATG AAC AGG GAG AAG AAA AAC AAA ATC        2450
Asn Ile Glu Pro Thr Asp Leu Met Asn Arg Glu Lys Lys Asn Lys Ile
            800                 805                 810

CCA AGT ATG CAA GTT GGG TTC ATA GAT GCC ATC TGC TTG CAA CTG TAT        2498
Pro Ser Met Gln Val Gly Phe Ile Asp Ala Ile Cys Leu Gln Leu Tyr
        815                 820                 825

GAG GCC CTG ACC CAC GTG TCA GAG GAC TGT TTC CCT TTG CTA GAT GGC        2546
Glu Ala Leu Thr His Val Ser Glu Asp Cys Phe Pro Leu Leu Asp Gly
830                 835                 840                 845

TGC AGA AAG AAC AGG CAG AAA TGG CAG GCC CTT GCA GAA CAG CAG GAG        2594
Cys Arg Lys Asn Arg Gln Lys Trp Gln Ala Leu Ala Glu Gln Gln Glu
            850                 855                 860

AAG ATG CTG ATT AAT GGG GAA AGC GGC CAG GCC AAG CGG AAC                2636
Lys Met Leu Ile Asn Gly Glu Ser Gly Gln Ala Lys Arg Asn
            865                 870                 875

TGACTCGAG                                                              2645
```

(2) INFORMATION FOR SEQ ID NO:23:

(i) SEQUENCE CHARACTERISTICS:
        (A) LENGTH: 875 amino acids
        (B) TYPE: amino acid
        (D) TOPOLOGY: linear (ii) MOLECULE TYPE: protein (xi) SEQUENCE DESCRIPTION: SEQ ID NO:23:

```
Met Glu Arg Ala Gly Pro Ser Phe Gly Gln Gln Arg Gln Gln Gln Gln
1               5                   10                  15

Pro Gln Gln Lys Gln Gln Gln Arg Asp Gln Asp Ser Val Glu Ala
            20                  25                  30

Trp Leu Asp Asp His Trp Asp Phe Thr Phe Ser Tyr Phe Val Arg Lys
        35                  40                  45

Ala Thr Arg Glu Met Val Asn Ala Trp Phe Ala Glu Arg Val His Thr
    50                  55                  60

Ile Pro Val Cys Lys Glu Gly Ile Arg Gly His Thr Glu Ser Cys Ser
65                  70                  75                  80

Cys Pro Leu Gln Gln Ser Pro Arg Ala Asp Asn Ser Val Pro Gly Thr
                85                  90                  95

Pro Thr Arg Lys Ile Ser Ala Ser Glu Phe Asp Arg Pro Leu Arg Pro
            100                 105                 110

Ile Val Val Lys Asp Ser Glu Gly Thr Val Ser Phe Leu Ser Asp Ser
        115                 120                 125

Glu Lys Lys Glu Gln Met Pro Leu Thr Pro Pro Arg Phe Asp His Asp
130                 135                 140

Glu Gly Asp Gln Cys Ser Arg Leu Leu Glu Leu Val Lys Asp Ile Ser
145                 150                 155                 160

Ser His Leu Asp Val Thr Ala Leu Cys His Lys Ile Phe Leu His Ile
                165                 170                 175

His Gly Leu Ile Ser Ala Asp Arg Tyr Ser Leu Phe Leu Val Cys Glu
            180                 185                 190

Asp Ser Ser Asn Asp Lys Phe Leu Ile Ser Arg Leu Phe Asp Val Ala
        195                 200                 205

Glu Gly Ser Thr Leu Glu Glu Val Ser Asn Asn Cys Ile Arg Leu Glu
210                 215                 220

Trp Asn Lys Gly Ile Val Gly His Val Ala Ala Leu Gly Glu Pro Leu
225                 230                 235                 240
```

```
Asn Ile Lys Asp Ala Tyr Glu Asp Pro Arg Phe Asn Ala Glu Val Asp
            245                 250                 255

Gln Ile Thr Gly Tyr Lys Thr Gln Ser Ile Leu Cys Met Pro Ile Lys
            260                 265                 270

Asn His Arg Glu Glu Val Val Gly Val Ala Gln Ala Ile Asn Lys Lys
            275                 280             285

Ser Gly Asn Gly Gly Thr Phe Thr Glu Lys Asp Glu Lys Asp Phe Ala
            290                 295                 300

Ala Tyr Leu Ala Phe Cys Gly Ile Val Leu His Asn Ala Gln Leu Tyr
305                     310                 315                 320

Glu Thr Ser Leu Leu Glu Asn Lys Arg Asn Gln Val Leu Leu Asp Leu
                    325                 330                 335

Ala Ser Leu Ile Phe Glu Glu Gln Gln Ser Leu Glu Val Ile Leu Lys
                340                 345                 350

Lys Ile Ala Ala Thr Ile Ile Ser Phe Met Gln Val Gln Lys Cys Thr
            355                 360                 365

Ile Phe Ile Val Asp Glu Asp Cys Ser Asp Ser Phe Ser Ser Val Phe
370                 375                 380

His Met Glu Cys Glu Glu Leu Glu Lys Ser Ser Asp Thr Leu Thr Arg
385                 390                 395                 400

Glu His Asp Ala Asn Lys Ile Asn Tyr Met Tyr Ala Gln Tyr Val Lys
                405                 410                 415

Asn Thr Met Glu Pro Leu Asn Ile Pro Asp Val Ser Lys Asp Lys Arg
                420                 425                 430

Phe Pro Trp Thr Thr Glu Asn Thr Gly Asn Val Asn Gln Gln Cys Ile
            435                 440                 445

Arg Ser Leu Leu Cys Thr Pro Ile Lys Asn Gly Lys Lys Asn Lys Val
            450                 455                 460

Ile Gly Val Cys Gln Leu Val Asn Lys Met Glu Glu Asn Thr Gly Lys
465                 470                 475                 480

Val Lys Pro Phe Asn Arg Asn Asp Glu Gln Phe Leu Glu Ala Phe Val
                485                 490                 495

Ile Phe Cys Gly Leu Gly Ile Gln Asn Thr Gln Met Tyr Glu Ala Val
                500                 505                 510

Glu Arg Ala Met Ala Lys Gln Met Val Thr Leu Glu Val Leu Ser Tyr
            515                 520                 525

His Ala Ser Ala Ala Glu Glu Glu Thr Arg Glu Leu Gln Ser Leu Ala
            530                 535                 540

Ala Ala Val Val Pro Ser Ala Gln Thr Leu Lys Ile Thr Asp Phe Ser
545                 550                 555                 560

Phe Ser Asp Phe Glu Leu Ser Asp Leu Glu Thr Ala Leu Cys Thr Ile
                565                 570                 575

Arg Met Phe Thr Asp Leu Asn Leu Val Gln Asn Phe Gln Met Lys His
            580                 585                 590

Glu Val Leu Cys Arg Trp Ile Leu Ser Val Lys Lys Asn Tyr Arg Lys
            595                 600                 605

Asn Val Ala Tyr His Asn Trp Arg His Ala Phe Asn Thr Ala Gln Cys
            610                 615                 620

Met Phe Ala Ala Leu Lys Ala Gly Lys Ile Gln Asn Lys Leu Thr Asp
625                 630                 635                 640

Leu Glu Ile Leu Ala Leu Leu Ile Ala Ala Leu Ser His Asp Leu Asp
                    645                 650                 655

His Arg Gly Val Asn Asn Ser Tyr Ile Gln Arg Ser Glu His Pro Leu
            660                 665                 670
```

```
Ala Gln Leu Tyr Cys His Ser Ile Met Glu His His His Phe Asp Gln
        675                 680                 685

Cys Leu Met Ile Leu Asn Ser Pro Gly Asn Gln Ile Leu Ser Gly Leu
        690                 695                 700

Ser Ile Glu Glu Tyr Lys Thr Thr Leu Lys Ile Ile Lys Gln Ala Ile
705                 710                 715                 720

Leu Ala Thr Asp Leu Ala Leu Tyr Ile Lys Arg Arg Gly Glu Phe Phe
            725                 730                 735

Glu Leu Ile Arg Lys Asn Gln Phe Asn Leu Glu Asp Pro His Gln Lys
            740                 745                 750

Glu Leu Phe Leu Ala Met Leu Met Thr Ala Cys Asp Leu Ser Ala Ile
        755                 760                 765

Thr Lys Pro Trp Pro Ile Gln Gln Arg Ile Ala Glu Leu Val Ala Thr
    770                 775                 780

Glu Phe Phe Asp Gln Gly Asp Arg Glu Arg Lys Glu Leu Asn Ile Glu
785                 790                 795                 800

Pro Thr Asp Leu Met Asn Arg Glu Lys Lys Asn Lys Ile Pro Ser Met
            805                 810                 815

Gln Val Gly Phe Ile Asp Ala Ile Cys Leu Gln Leu Tyr Glu Ala Leu
            820                 825                 830

Thr His Val Ser Glu Asp Cys Phe Pro Leu Leu Asp Gly Cys Arg Lys
        835                 840                 845

Asn Arg Gln Lys Trp Gln Ala Leu Ala Glu Gln Gln Glu Lys Met Leu
    850                 855                 860

Ile Asn Gly Glu Ser Gly Gln Ala Lys Arg Asn
865                 870                 875
```

ANTIBODIES TO CGMP-BINDING, CGMP-SPECIFIC PHOSPODIESTERASE

This is a Rule 60 divisional of U.S. patent application Ser. No. 08/250,847, filed May 27, 1994, which in turn is a continuation-in-part of U.S. patent application Ser. No. 08/068,051, filed May 27, 1993 now abandoned.

Experimental work described herein was supported in part by Research Grants GM15731, DK21723, DK40029 and GM41269 and the Medical Scientist Training Program Grant GM07347 awarded by the National Institutes of Health. The United States government has certain rights in the invention.

FIELD OF THE INVENTION

The present invention relates generally to a cyclic guanosine monophosphate-binding, cyclic guanosine monophosphate-specific phosphodiesterase designated cGB-PDE and more particularly to novel purified and isolated polynucleotides encoding cGB-PDE polypeptides, to methods and materials for recombinant production of cGB-PDE polypeptides, and to methods for identifying modulators of cGB-PDE activity.

BACKGROUND

Cyclic nucleotide phosphodiesterases (PDEs) that catalyze the hydrolysis of 3'5' cyclic nucleotides such as cyclic guanosine monophosphate (cGMP) and cyclic adenosine monophosphate (cAMP) to the corresponding nucleoside 5' monophosphates constitute a complex family of enzymes. By mediating the intracellular concentration of the cyclic nucleotides, the PDE isoenzymes function in signal transduction pathways involving cyclic nucleotide second messengers.

A variety of PDEs have been isolated from different tissue sources and many of the PDEs characterized to date exhibit differences in biological properties including physicochemical properties, substrate specificity, sensitivity to inhibitors, immunological reactivity and mode of regulation. [See Beavo et al., *Cyclic Nucleotide Phosphodiesterases: Structure, Regulation and Drug Action*, John Wiley & Sons, Chichester, U.K. (1990).] Comparison of the known amino acid sequences of various PDEs indicates that most PDEs are chimeric multidomain proteins that have distinct catalytic and regulatory domains. [See Charbonneau, pp. 267–296 in Beavo et al., supra] All mammalian PDEs characterized to date share a sequence of approximately 250 amino acid residues in length that appears to comprise the catalytic site and is located in the carboxyl terminal region of the enzyme. PDE domains that interact with allosteric or regulatory molecules are thought to be located within the amino-terminal regions of the isoenzymes. Based on their biological properties, the PDEs may be classified into six general families: the $Ca^{2+}$/calmodulin-stimulated PDEs (Type I), the cGMP-stimulated PDEs (Type II), the cGMP-inhibited PDEs (Type III), the cAMP-specific PDEs (Type IV), the cGMP-specific phosphodiesterase cGB-PDE (Type V) which is the subject of the present invention and the cGMP-specific photoreceptor PDEs (Type VI).

The cGMP-binding PDEs (Type II, Type V and Type VI PDEs), in addition to having a homologous catalytic domain near their carboxyl terminus, have a second conserved sequence which is located closer to their amino terminus and which may comprise an allosteric cGMP-binding domain. See Charbonneau et al., *Proc. Natl. Acad. Sci. USA*, 87: 288–292 (1990).

The Type II cGMP-stimulated PDEs (cGs-PDEs) are widely distributed in different tissue types and are thought to exist as homodimers of 100–105 kDa subunits. The cGs-PDEs respond under physiological conditions to elevated cGMP concentrations by increasing the rate of cAMP hydrolysis. The amino acid sequence of a bovine heart cGs-PDE and a partial cDNA sequence of a bovine adrenal cortex cGS-PDE are reported in LeTrong et al., *Biochmistry*, 29: 10280–10288 (1990) and full length bovine adrenal and human fetal brain cGB-PDE cDNA sequences are described in Patent Cooperation Treaty International Publication No. WO 92/18541 published on Oct. 29, 1992. The full length bovine adrenal cDNA sequence is also described in Sonnenburg et al., *J. Biol. Chem.*, 266: 17655–17661 (1991).

The photoreceptor PDEs and the cGB-PDE have been described as cGMP-specific PDEs because they exhibit a 50-fold or greater selectivity for hydrolyzing cGMP over cAMP.

The photoreceptor PDEs are the rod outer segment PDE (ROS-PDE) and the cone PDE (COS-PDE). The holoenzyme structure of the ROS-PDE consists of two large subunits α (88 kDa) and β (84 kDa) which are both catalytically active and two smaller γ regulatory subunits (both 11 kDa). A soluble form of the ROS-PDE has also been identified which includes α, β, and γ subunits and a δ subunit (15 kDa) that appears to be identical to the COS-PDE 15 kDa subunit. A full-length cDNA corresponding to the bovine membrane-associated ROS-PDE α subunit is described in Ovchinnikov et al., *FEBS Lett.*, 223: 169–173 (1987) and a full length cDNA corresponding to the bovine rod outer segment PDE β subunit is described in Lipkin et al., *J. Biol. Chem.*, 265: 12955–12959 (1990). Ovchinnikov et al., *FEBS Lett.*, 204: 169–173 (1986) presents a full-length cDNA corresponding to the bovine ROS-PDE γ subunit and the amino acid sequence of the δ subunit. Expression of the ROS-PDE has also been reported in brain in Coflins et al., *Genomics*, 13: 698–704 (1992). The COS-PDE is composed of two identical α' (94 kDa) subunits and three smaller subunits of 11 kDa, 13 kDa and 15 kDa. A full-length cDNA corresponding to the bovine COS-PDE α' subunit is reported in Li et al., *Proc. Natl. Acad. Sci. USA*, 87: 293–297 (1990).

cGB-PDE has been purified to homogeneity from rat [Francis et al., *Methods Enzymol.*, 159: 722–729 (1988)] and bovine lung tissue [Thomas et al., *J. Biol. Chem.*, 265: 14964–14970 (1990), hereinafter "Thomas I"]. The presence of this or similar enzymes has been reported in a variety of tissues and species including rat and human platelets [Hamet et al., *Adv. Cyclic Nucleotide Protein Phosphorylaton Res.*, 16: 119–136 (1984)], rat spleen [Coquil et al., *Biochem. Biophys. Res. Commun.*, 127: 226–231 (1985)], guinea pig lung [Davis et al., *J. Biol. Chem.*, 252: 4078–4084 (1977)], vascular smooth muscle [Coquil et al., *Biochim. Biophys. Acta*, 631: 148–165 (1980)], and sea urchin sperm [Francis et al., *J. Biol. Chem.*, 255: 620–626 (1979)]. cGB-PDE may be a homodimer comprised of two 93 kDa subunits. [See Thomas I, supra] cGB-PDE has been shown to contain a single site not found in other known cGMP-binding PDEs which is phosphorylated by cGMP-dependent protein kinase (cGK) and, with a lower affinity, by cAMP-dependent protein kinase (cAK). [See Thomas et al., *J. Biol. Chem.*, 265: 14971–14978 (1990), hereinafter "Thomas II"] The primary amino acid sequence of the phosphorylation site and of the amino-terminal end of a fragment generated by chymotryptic digestion of cGB-PDE are described in Thomas II, supra, and Thomas I, supra, respectively. However, the majority of the amino acid sequence of cGB-PDE has not previously been described.

Various inhibitors of different types of PDEs have been described in the literature. Two inhibitors that exhibit some specificity for Type V PDEs are zaprinast and dipyridamole. See Francis et al., pp. 117–140 in Beavo et al., supra.

Elucidation of the DNA and amino acid sequences encoding the cGB-PDE and production of cGB-PDE polypeptide by recombinant methods would provide information and material to allow the identification of novel agents that selectively modulate the activity of the cGB-PDEs. The recognition that there are distinct types or families of PDE isoenzymes and that different tissues express different complements of PDEs has led to an interest in the development of PDE modulators which may have therapeutic indications for disease states that involve signal transduction pathways utilizing cyclic nucleotides as second messengers. Various selective and non-selective inhibitors of PDE activity are discussed in Murray et al., *Biochm. Soc. Trans.*, 20(2): 460–464 (1992). Development of PDE modulators without the ability to produce a specific PDE by recombinant DNA techniques is difficult because all PDEs catalyze the same basic reaction, have overlapping substrate specificities and occur only in trace amounts. As a result, purification to homogeneity of many PDEs is a tedious and difficult process.

There thus continues to exist a need in the art for DNA and amino acid sequence information for the cGB-PDE, for methods and materials for the recombinant production of cGB-PDE polypeptides and for methods for identifying specific modulators of cGB-PDE activity.

SUMMARY OF THE INVENTION

The present invention provides novel purified and isolated polynucleotides (e.g., DNA sequences and RNA transcripts, both sense and antisense strands, including splicevariants thereof) encoding the cGMP-binding, cGMP-specific PDE designated cGB-PDE. Preferred DNA sequences of the invention include genomic and cDNA sequences as well as wholly or partially chemically synthesized DNA sequences. DNA sequences encoding cGB-PDE that are set out in SEQ ID NO: 9 or 20 and DNA sequences which hybridize thereto under stringent conditions or DNA sequences which would hybridize thereto but for the redundancy of the genetic code are contemplated by the invention. Also contemplated by the invention are biological replicas (i.e., copies of isolated DNA sequences made in vivo or in vitro) of DNA sequences of the invention. Autonomously replicating recombinant constructions such as plasmid and viral DNA vectors incorporating cGB-PDE sequences and especially vectors wherein DNA encoding cGB-PDE is operatively linked to an endogenous or exogenous expression control DNA sequence and a transcriptional terminator are also provided. Specifically illustrating expression plasmids of the invention is the plasmid hcgbmet156-2 6n in *E. coli* strain JM109 which was deposited with the American Type Culture Collection (ATCC), 12301 Parklawn Drive, Rockville, Md. 20852, on May 4, 1993 as Accession No. 69296.

According to another aspect of the invention, host cells including procaryotic and eucaryotic cells, are stably transformed with DNA sequences of the invention in a manner allowing the desired polypeptides to be expressed therein. Host cells expressing cGB-PDE products can serve a variety of useful purposes. Such cells constitute a valuable source of immunogen for the development of antibody substances specifically immunoreactive with cGB-PDE. Host cells of the invention are conspicuously useful in methods for the large scale production of cGB-PDE polypeptides wherein the cells are grown in a suitable culture medium and the desired polypeptide products are isolated from the cells or from the medium in which the cells are grown by, for example, immunoaffinity purification.

cGB-PDE products may be obtained as isolates from natural cell sources or may be chemically synthesized, but are preferably produced by recombinant procedures involving host cells of the invention. Use of mammalian host cells is expected to provide for such post-translational modifications (e.g., glycosylation, truncation, lipidation and tyrosine, serine or threonine phosphorylation) as may be needed to confer optimal biological activity on recombinant expression products of the invention. cGB-PDE products of the invention may be full length polypeptides, fragments or variants. Variants may comprise cGB-PDE polypeptide analogs wherein one or more of the specified (i.e., naturally encoded) amino acids is deleted or replaced or wherein one or more nonspecified amino acids are added: (1) without loss of one or more of the biological activities or immunological characteristics specific for cGB-PDE; or (2) with specific disablement of a particular biological activity of cGB-PDE.

Also comprehended by the present invention are antibody substances (e.g., monoclonal and polyclonal antibodies, single chain antibodies, chimeric antibodies, CDR-grafted antibodies and the like) and other binding proteins specific for cGB-PDE. Specific binding proteins can be developed using isolated or recombinant cGB-PDE or cGB-PDE variants or cells expressing such products. Binding proteins are useful, in turn, in compositions for immunization as well as for purifying cGB-PDE polypeptides and detection or quantification of cGB-PDE polypeptides in fluid and tissue samples by known immunogical procedures. They are also manifestly useful in modulating (i.e., blocking, inhibiting or stimulating) biochemical activities of cGB-PDE, especially those activities involved in signal transduction. Anti-idiotypic antibodies specific for anti-cGB-PDE antibody substances are also contemplated.

The scientific value of the information contributed through the disclosures of DNA and amino acid sequences of the present invention is manifest. As one series of examples, knowledge of the sequence of a cDNA for cGB-PDE makes possible the isolation by DNA/DNA hybridization of genomic DNA sequences encoding cGB-PDE and specifying cGB-PDE expression control regulatory sequences such as promoters, operators and the like. DNA/DNA hybridization procedures carried out with DNA sequences of the invention under stringent conditions are likewise expected to allow the isolation of DNAs encoding allelic variants of cGB-PDE, other structurally related proteins sharing one or more of the biochemical and/or immunological properties specific to cGB-PDE, and non-human species proteins homologous to cGB-PDE. Polynucleotides of the invention when suitably labelled are useful in hybridization assays to detect the capacity of cells to synthesize cGB-PDE. Polynucleotides of the invention may also be the basis for diagnostic methods useful for identifying a genetic alteration(s) in the cGB-PDE locus that underlies a disease state or states. Also made available by the invention are anti-sense polynucleotides relevant to regulating expression of cGB-PDE by those cells which ordinarily express the same.

The DNA and amino acid sequence information provided by the present invention also makes possible the systematic analysis of the structure and function of cGB-PDE and definition of those molecules with which it will interact. Agents that modulate cGB-PDE activity may be identified by incubating a putative modulator with lysate from eucaryotic cells expressing recombinant cGB-PDE and determining the effect of the putative modulator on cGB-PDE phosphodiesterase activity. In a preferred embodiment the eucaryotic cell lacks endogenous cyclic nucleotide phosphodiesterase activity. Specifically illustrating such a eucaryotic cell is the yeast strain YKS45 which was deposited with the ATCC on May 19, 1993 as Accession No. 74225. The selectivity of a compound that modulates the activity of the cGB-PDE can be evaluated by comparing its activity on the cGB-PDE to its activity on other PDE isozymes. The combination of the recombinant cGB-PDE products of the invention with other recombinant PDE products in a series of independent assays provides a system for developing selective modulators of cGB-PDE.

Selective modulators may include, for example, antibodies and other proteins or peptides which specifically bind to the cGB-PDE or cGB-PDE nucleic acid, oligonucleotides which specifically bind to the cGB-PDE or cGB-PDE nucleic acid and other non-peptide compounds (e.g., isloated or synthetic organic molecules) which specifically react with cGB-PDE or cGB-PDE nucleic acid. Mutant forms of cGB-PDE which affect the enzymatic activity or cellular localization of the wild-type cGB-PDE are also contemplated by the invention. Presently preferred targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the phosphorylation site(s) of cGB-PDE and (5) the regions of the cGB-PDE which are involved in dimerization of cGB-PDE subunits. Modulators of cGB-PDE activity may be therapeutically useful in treatment of a wide range of diseases and physiological conditions.

BRIEF DESCRIPTION OF THE DRAWINGS

Numerous other aspects and advantages of the present invention will be apparent upon consideration of the following detailed description thereof, reference being made to the drawing wherein:

FIGS. 1A 1B and 1C shown is an alignment of the conserved catalytic domains of several PDE isoenzymes wherein residues which are identical in all PDEs listed are indicated by their one letter amino acid abbreviation in the "conserved" line, residues which are identical in the cGB-PDE and photoreceptor PDEs only are indicated by a star in the "conserved" line and gaps introduced for optimum alignment are indicated by periods;

FIGS. 2A 2B, and 2C show is an alignment of the cGMP-binding domains of several PDE isoenzymes wherein residues which are identical in all PDEs listed are indicated by their one letter amino acid abbreviation in the "conserved" line and gaps introduced for optimum alignment are indicated by periods;

FIG. 3 is an alignment of internally homologous repeats from several PDE isoenzymes wherein residues identical in each repeat A and B from all cGMP-binding PDEs listed are indicated by their one letter amino acid abbreviation in the "conserved" line and stars in the "conserved" line represent positions in which all residues are chemically conserved;

DETAILED DESCRIPTION

Figure 4:
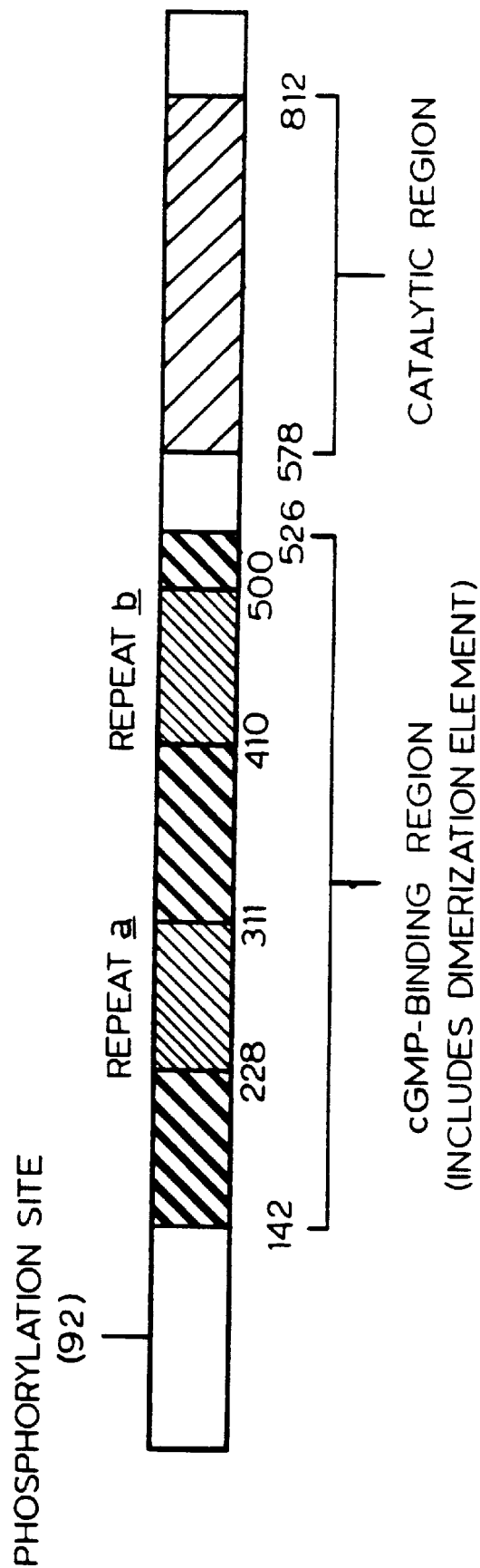
FIG. 4 schematically depicts the domain organization of cGB-PDE.

The following examples illustrate the invention. Example 1 describes the isolation of a bovine cGB-PDE cDNA fragment by PCR and subsequent isolation of a full length cGB-PDE cDNA using the PCR fragment as a probe. Example 2 presents an analysis of the relationship of the bovine cGB-PDE amino acid sequence to sequences reported for various other PDEs. Northern blot analysis of cGB-PDE mRNA in various bovine tissues is presented in Example 3. Expression of the bovine cGB-PDE cDNA in COS cells is described in Example 4. Example 5 presents results of assays of the cGB-PDE COS cell expression product for phosphodiesterase activity, cGMP-binding activity and $Zn^{2+}$ hydrolase activity. Example 6 describes the isolation of human cDNAs homologous to the bovine cGB-PDE cDNA. The expression of a human cGB-PDE cDNA in yeast cells is presented in Example 7. RNase protection assays to detect cGB-PDE in human tissues are described in Example 8. Example 9 describes the bacterial expression of human cGB-PDE cDNA and the development of antibodies reactive with the bacterial cGB-PDE expression product. Example 10 describes cGB-PDE analogs and fragments. The generation of monoclonal antibodies that recognize cGB-PDE is described in Example 11. Example 12 relates to utillizing recombinant cGB-PDE products of the invention to develop agents that selectively modulate the biological activities of cGB-PDE.

EXAMPLE 1

The polymerase chain reaction (PCR) was utilized to isolate a cDNA fragment encoding a portion of cGB-PDE from bovine lung first strand cDNA. Fully degenerate sense and antisense PCR primers were designed based on the partial cGB-PDE amino acid sequence described in Thomas I, supra, and novel partial amino acid sequence information.

A. Purification of cGB-PDE Protein cGB-PDE was purified as described in Thomas I, supra, or by a modification of that method as described below.

Fresh bovine lungs (5–10 kg) were obtained from a slaughterhouse and immediately placed on ice. The tissue was ground and combined with cold PEM buffer (20 mM sodium phosphate, pH 6.8, containing 2 mM EDTA and 25 mM β-mercaptoethanol). After homogenization and centrifugation, the resulting supernatant was incubated with 4–7 liters of DEAE-cellulose (Whatman, UK) for 3–4 hours. The DEAE slurry was then filtered under vacuum and rinsed with multiple volumes of cold PEM. The resin was poured into a glass column and washed with three to four volumes of PEM. The protein was eluted with 100 mM NaCl in PEM and twelve 1-liter fractions were collected. Fractions were assayed for IBMX-stimulated cGMP binding and cGMP phosphodiesterase activities by standard procedures described in Thomas et al., supra. Appropriate fractions were pooled, diluted 2-fold with cold, deionized water and subjected to Blue Sepharose1® CL-6B (Pharmacia LKB Biotechnology Inc., Piscataway, N.J.) chromatography. Zinc chelate affinity adsorbent chromatography was then performed using either an agarose or Sepharose-based gel matrix. The resulting protein pool from the zinc chelation step treated as described in the Thomas I, supra, or was subjected to a modified purification procedure.

As described in Thomas I, supra, the protein pool was applied in multiple loads to an HPLC Bio-Sil TSK-545 DEAE column (150×21.5 mm) (BioRad Laboratories, Hercules, Calif.) equilibrated in PEM at 4° C. After an equilibration period, a 120-ml wash of 50 mM NaCl in PEM was followed by a 120-ml linear gradient (50–200 mM NaCl in PEM) elution at a flow rate of 2 ml/minute. Appropriate fractions were pooled and concentrated in dialysis tubing against Sephadex G-200 (Boehringer Mannheim Biochemicals, UK) to a final volume of 1.5 ml. The concentrated cGB-PDE pool was applied to an HPLC gel filtration column (Bio-Sil TSK-250, 500×21.5 mm) equilibrated in 100 mM sodium phosphate, pH 6.8, 2 mM EDTA, 25 mM β-mercaptoethanol and eluted with a flow rate of 2 ml/minute at 4° C.

If the modified, less cumbersome procedure was performed, the protein pool was dialyzed against PEM for 2 hours and loaded onto a 10 ml preparative DEAE Sephacel column (Pharmacia) equilibrated in PEM buffer. The protein was eluted batchwise with 0.5M NaCl in PEM, resulting in an approximately 10–15 fold concentration of protein. The concentrated protein sample was loaded onto an 800 ml (2.5 cm×154 cm) Sephacryl S400 gel filtration column (Boehringer) equilibrated in 0.1M NaCl in PEM, and eluted at a flow rate of 1.7 ml/minute.

The purity of the protein was assessed by Coomassie staining after sodium dodecyl sulfate-polyacrylamide gel electrophoresis (SDS-PAGE). Approximately 0.5–3.0 mg of pure cGB-PDE were obtained per 10 kg bovine lung.

Rabbit polyclonal antibodies specific for the purified bovine cGB-PDE were generated by standard procedures.

B. Amino Acid Sequencing of cGB-PDE cGB-PDE phosphorylated with [$^{32}$P]ATP and was then digested with protease to yield $^{32}$P-labelled phosphopeptides. Approximately 100 μg of purified cGB-PDE was phosphorylated in a reaction mixture containing 9mM MgCl$_2$, 9 μM [$^{32}$P]ATP, 10 μM cGMP, and 4.2 μg purified bovine catalytic subunit of cAMP-dependent protein kinase (cAK) in a final volume of 900 μl. Catalytic subunit of cAK was prepared according to the method of Flockhart et al., pp. 209–215 in Marangos et al., Brain Receptor Methodologies, Part A, Academic Press, Orlando, Fla. (1984). The reaction was incubated for 30 minutes at 30° C., and stopped by addition of 60 μl of 200 mM EDTA.

To obtain a first peptide sequence from cGB-PDE, 3.7 μl of a 1 mg/ml solution of a α-chymotrypsin in KPE buffer (10 mM potassium phosphate, pH 6.8, with 2 mM EDTA) was added to 100 μg purified, phosphorylated cGB-PDE and the mixture was incubated for 30 minutes at 30° C. Proteolysis was stopped by addition of 50 μl of 10% SDS and 25 μl of β-mercaptoethanol. The sample was boiled until the volume was reduced to less than 400 μl, and was loaded onto an 8% preparative SDS-polyacrylamide gel and subjected to electrophoresis at 50 mAmps. The separated digestion products were electroblotted onto Immobilon polyvinylidene difluoride (Millipore, Bedford, Mass.), according to the method of Matsudaira, J. Biol. Chem, 262: 10035–10038 (1987). Transferred protein was identified by Coomassie Blue staining, and a 50 kDa band was excised from the membrane for automated gas-phase amino acid sequencing. The sequence of the peptide obtained by the α-chymotryptic digestion procedure is set out below as SEQ ID NO: 1.

SEQ ID NO: 1

REXDANRINYMYAQYVKNTM

A second sequence was obtained from a cGB-PDE peptide fragment generated by V8 proteolysis. Approximately 200 μg of purified cGB-PDE was added to 10 mM MgCl$_2$, 10 μM [$^{32}$P]ATP, 100 μM cGMP, and 1 μg/ml purified catalytic subunit of cAK in a final volume of 1.4 ml. The reaction was incubated for 30 minutes at 30° C., and was terminated by the addition of 160 μl of 0.2M EDTA. Next, 9 μl of 1 mg/ml *Staphylococcal aureus* V8 protease (International Chemical Nuclear Biomedicals, Costa Mesa, Calif.) diluted in KPE was added, followed by a 15 minute incubation at 30° C. Proteolysis was stopped by addition of 88 μl of 10% SDS and 45 μl β-mercaptoethanol. The digestion products were separated by electrophoresis on a preparative 10% SDS-polyacrylamide gel run at 25 mAmps for 4.5 hours. Proteins were electroblotted and stained as described above. A 28 kDa protein band was excised from the membrane and subjected to automated gas-phase amino acid sequencing. The sequence obtained is set out below as SEQ ID NO: 2.

SEQ ID NO: 2

QSLAAAVVP

C. PCR Amplification of Bovine cDNA

The partial amino acid sequences utilized to design primers (SEQ ID NO: 3, below, and amino acids 9–20 of SEQ ID NO: 1) and the sequences of the corresponding PCR primers (in IUPAC nomenclature) are set below wherein SEQ ID NO: 3 is the sequence reported in Thomas I, supra.

```
SEQ ID NO: 3

F    D    N    D    E    G    E    Q

5' TTY  GAY  AAY  GAY  GAR  GGN  GAR  CA 3'   (SEQ ID NO: 4)

3' AAR  CTR  TTR  CTR  CTY  CCN  CTY  GT 5'   (SEQ ID NO: 5)

SEQ ID NO: 1, Amino acids 9-20

N    Y    M    Y    A    Q    Y    V    K    N    T    M

5' AAY  TAY  ATG  TAY  GCN  CAR  TAY  GT 3'   (SEQ ID NO: 6)
```

```
3' TTR ATR TAC ATR CGN GTY ATR CA 5' (SEQ ID NO: 7)

3' TTR ATR TAC ATR CGN GTY ATR CAN TTY TTR TGN TAC 5'
  (SEQ ID NO: 8)
```

The sense and antisense primers, synthesized using an Applied Biosystems Model 380A DNA Synthesizer (Foster City, Calif.), were used in all possible combinations to amplify cGB-PDE-specific sequences from bovine lung first strand cDNA as described below.

After ethanol precipitation, pairs of oligonucleotides were combined (SEQ ID NO: 4 or 5 combined with SEQ ID NOs: 6, 7 or 8) at 400 nM each in a PCR reaction. The reaction was run using 50 ng first strand bovine lung cDNA (generated using AMV reverse transcriptase and random primers on oligo dT selected bovine lung mRNA), 200 µM dNTPs, and 2 units of Taq polymerase. The initial denaturation step was carried out at 94° C. for 5 minutes, followed by 30 cycles of a 1 minute denaturation step at 94° C., a two minute annealing step at 50° C., and a 2 minute extension step at 72° C. PCR was performed using a Hybaid Thermal Reactor (ENK Scientific Products, Saratoga, Calif.) and products were separated by gel electrophoresis on a 1% low melting point agarose gel run in 40 mM Tris-acetate, 2mM EDTA. A weak band of about 800–840 bp was seen with the primers set out in SEQ ID NOs: 4 and 7 and with primers set out in SEQ ID NOs: 4 and 8. None of the other primer pairs yielded visible bands. The PCR product generated by amplification with the primers set out in SEQ ID NOs: 4 and 7 was isolated using the Gene Cleans® (Bio101, La Jolla, Calif.) DNA purification kit according to the manufacturer's protocol. The PCR product (20 ng) was ligated into 200 ng of linearized pBluescript KS(+) (Stratagene, La Jolla, Calif.), and the resulting plasmid construct was used to transform E. coli XL1 Blue cells (Stratagene Cloning Systems, La Jolla, Calif.). Putative transformation positives were screened by sequencing. The sequences obtained were not homologous to any known PDE sequence or to the known partial cGB-PDE sequences.

PCR was performed again on bovine lung first strand cDNA using the primers set out in SEQ ID NOs: 4 and 7. A clone contag a 0.8 Kb insert with a single large open reading frame was identified. The open reading frame encoded a polypeptide that included the amino acids KNTM (amino acids 17–20 of SEQ ID NO: 1 which were not utilized to design the primer sequence which is set out in SEQ ID NO: 7) and that possessed a high degree of homology to the deduced amino acid sequences of the cGs-, ROS- and COS-PDEs. The clone identified corresponds to nucleotides 489–1312 of SEQ ID NO: 9.

D. Construction and Hybridization Screening of a Bovine cDNA Library

In order to obtain a cDNA encoding a full-length cGB-PDE, a bovine lung cDNA library was screened using the $^{32}$P-labelled PCR-generated cDNA insert as a probe.

Polyadenylated RNA was prepared from bovine lung as described Sonnenburg et al., J. Biol. Chem., 266: 17655–17661 (1991). First strand cDNA was synthesized using AMV reverse transcriptase (Life Sciences, St. Petersburg, Fla.) with random hexanucleotide primers as described in Ausubel et al., Current Protocols in Molecular Biology, John Wiley & Sons, New York (1987). Second strand cDNA was synthesized using E. coli DNA polymerase I in the presence of E. coli DNA ligase and E. coli RNAse H. Selection of cDNAs larger than 500 bp was performed by Sepharose® CL4B (Millipore) chromatography. EcoRI adaptors (Promega, Madison, Wis.) were ligated to the cDNA using T4 DNA ligase. Following heat inactivation of the ligase, the cDNA was phosphorylated using T4 polynucleotide kinase. Unligated adaptors were removed by Sepharosed® CL-4B chromatography (Pharmacia, Piscataway, N.J.). The cDNA was ligated into EcoRI-digested, dephosphorylated lambda Zap®II arms (Stratagene) and packaged with Gigapack® Gold (Stratagene) extracts according to the manufacturer's protocol. The titer of the unamplified library was $9.9 \times 10^5$ with 18% nonrecombinants. The library was amplified by plating 50,000 plaque forming units (pfu) on to twenty 150 mm plates, resulting in a final titer of $5.95 \times 10^6$ pfu/ml with 21% nonrecombinants.

The library was plated on twenty-four 150 mm plates at 50,000 pfu/plate, and screened with the $^{32}$P-labelled cDNA clone. The probe was prepared using the method of Feinberg et al., Anal. Biochem., 137: 266–267 (1984), and the $^{32}$P-labelled DNA was purified using Elutip-D® columns (Schleicher and Schuell Inc., Keene, N.H.) using the manufacturer's protocol. Plaque-lifts were performed using 15 cm nitrocellulose filters. Following denaturation and neutrlization, DNA was fixed onto the filters by baking at 80° C. for 2 hours. Hybridization was carried out at 42° C. overnight in a solution containing 50% formamide, 5× SSC (0.75M NaCl, 0.75M sodium citrate, pH 7), 25 mM sodium phosphate (pH 7.0), 2X Denhardt's solution, 10% dextran sulfate, 90 µg/ml yeast tRNA, and approximately $10^6$ cpm/ml $^{32}$P-labelled probe ($5 \times 10^8$ cpm/µg). The filters were washed twice in 0.1× SSC, 0.1% SDS at room temperature for 15 minutes per wash, followed by a single 20 minute wash in 0.1× SSC, 1% SDS at 45° C. The filters were then exposed to X-ray film at −70° C. for several days.

Plaques that hybridized with the labelled probe were purified by several rounds of replating and rescreening. Insert cDNAs were subcloned into the pBluescript SK(−) vector (Stratagene) by the in vivo excision method described by the manufacturer's protocol. Southern blots were performed in order to verify that the rescued cDNA hybridized to the PCR probe. Putative cGB-PDE cDNAs were sequenced using Sequenasel® Version 2.0 (United States Biochemical Corporation, Cleveland, Ohio) or TaqTrack® kits (Promega).

Three distinct cDNA clones designated cGB-2, cGB-8 and cGB-10 were isolated. The DNA and deduced amino acid sequences of clone cGB-8 are set out in SEQ ID NOs: 9 and 10. The DNA sequence downstream of nucleotide 2686 may represent a cloning artifact. The DNA sequence of cGB-10 is identical to the sequence of cGB-8 with the exception of one nucleotide. The DNA sequence of clone cGB-2 diverges from that of clone cGB-8 5' to nucleotide 219 of clone cgb-8 (see SEQ ID NO: 9) and could encode a protein with a different amino terminus.

The cGB-8 cDNA clone is 4474 bp in length and contains a large open reading frame of 2625 bp. The triplet ATG at position 99–101 in the nucleotide sequence is predicted to be the translation initiation site of the cGB-PDE gene because it is preceded by an in-frame stop codon and the surrounding bases are compatible with the Kozak consensus initiation site for eucaryotic mRNAs. The stop codon TAG is located at positions 2724–2726, and is followed by 1748 bp of 3' untranslated sequence. The sequence of cGB-8 does not contain a transcription termination consensus sequence, therefore the clone may not represent the entire 3' untranslated region of the corresponding mRNA.

The open reading frame of the cGB-8 cDNA encodes an 875 amino acid polypeptide with a calculated molecular mass of 99.5 kD. This calculated molecular mass is only slightly larger than the reported molecular mass of purified cGB-PDE, estimated by SDS-PAGE analysis to be approximately 93 kDa. The deduced amino acid sequence of cGB-8 corresponded exactly to all peptide sequences obtained from purified bovine lung cGB-PDE providing strong evidence that cGB-8 encodes cGB-PDE.

EXAMPLE 2

A search of the SWISS-PROT and GEnEmbl data banks (Release of February, 1992) conducted using the FASTA program supplied with the Genetics Computer Group (GCG) Software Package (Madison, Wis.) revealed that only DNA and amino acid sequences reported for other PDEs displayed significant similarity to the DNA and deduced amino acid of clone cGB-8.

Parrwise comparisons of the cGB-PDE deduced amino acid sequence with the sequences of eight other PDEs were conducted using the ALIGN [Dayhoff et al, *Methods Enzymol.*, 92: 524–545 (1983)] and BESTFTT [Wilbur et al., *Proc. Natl. Acad. Sci. USA*, 80: 726–730 (1983)] programs. Like all mammalian phosphodiesterases sequenced to date, cGB-PDE contains a conserved catalytic domain sequence of approximately 250 amino acids in the carboxyl-terminal half of the protein that is thought to be essential for catalytic activity. This segment comprises amino acids 578–812 of SEQ ID NO: 9 and exhibits sequence conservation with the corresponding regions of other PDEs. Table 1 below sets out the specific identity values obtained in pairwise comparisons of other PDEs with amino acids 578–812 of cGB-PDE, wherein "ratdunce" is the rat cAMP-specific PDE; "61 kCaM" is the bovine 61 kDa calcium/calmodulin-dependent PDE; "63 kCaM" is the bovine 63 kDa calcium/calmodulin-dependent PDE; "drosdunce" is the drosophila cAMP-specific dunce PDE; "ROS-α" is the bovine ROS-PDE α-subunit; "ROS-β" is the bovine ROS-PDEβ-subunit; "COS-α'" is the bovine COS-PDEα' subunit; and "cGs" is the bovine cGs-PDE (612–844).

TABLE 1

| Phosphodiesterase | Catalytic Domain Residues | % Identity |
| --- | --- | --- |
| Ratdunce | 77–316 | 31 |
| 61 kCaM | 193–422 | 29 |
| 63 kcam | 195–424 | 29 |
| drosdunce | 1–239 | 28 |
| ROS-α | 535–778 | 45 |
| ROS-β | 533–776 | 46 |
| COS-α' | 533–776 | 48 |
| cGs | 612–844 | 40 |

Multiple sequence alignments were performed using the Progressive Alignment Algorithm [eng et al., *Methods EnzymoL*, 183: 375–387 (1990)] implemented in the PILEUP program (GCG Software). FIG. 1A to 1C shows a multiple sequence alignment of the proposed catalytic domain of cGB-PDE with the all the corresponding regions of the PDEs of Table 1. Twenty-eight residues (see residues indicated by one letter amino acid abbreviations in the "conserved" line on FIG. 1A to 1C) are invariant among the isoenzymes including several conserved histidine residues predicted to play a functional role in catalysis. See Charbonneau et al., *Proc. Natl. Acad. Sci. USA*, supra. The catalytic domain of cGB-PDE more closely resembles the catalytic domains of the ROS-PDEs and COS-PDEs than the corresponding regions of other PDE isoenzymes. There are several conserved regions among the photoreceptor PDE and cGB-PDE that are not shared by other PDEs. Amino acid positions in these regions that are invariant in the photoreceptor PDE and cGB-PDE sequences are indicated by stars in the "conserved" line of FIG. 1A to 1C. Regions of homology among cGB-PDE and the ROS- and COS-PDEs may serve important roles in conferring specificity for cGMP hydrolysis relative to cAMP hydrolysis or for sensitivity to specific pharmacological agents.

Sequence similarity between cGB-PDE, cGs-PDE and the photoreceptor PDEs, is not limited to the conserved catalytic domain but also includes the noncatalytic cGMP binding domain in the amino-terminal half of the protein. Optimization of the alignment between cGB-PDE, cGs-PDE and the photoreceptor PDEs indicates that an amino-terminal conserved segment may exist including amino acids 142–526 of SEQ ID NO: 9. Pairwise analysis of the sequence of the proposed cGMP-binding domain of cGB-PDE with the corresponding regions of the photoreceptor PDEs and cGs-PDE revealed 26–28% sequence identity. Multiple sequence alignment of the proposed cGMP-binding domains with the cGMP-binding PDEs is shown in FIG. 2A to 2C wherein abbreviations are the same as indicated for Table 1. Thirty-eight positions in this nonctalytic domain appear to be invariant among all cGMP-binding PDEs (see positions indicated by one letter amino acid abbreviations in the "conserved" line of FIG. 2A to 2C).

The cGMP-binding domain of the cGMP-binding PDEs contains internally homologous repeats which may form two similar but distinct inter- or intra-subunit cGMP-binding sites. FIG. 3 shows a multiple sequence alignment of the repeats a (corresponding to amino acids 228–311 of cGB-PDE) and b (corresponding to amino acids 410–500 of cGB-PDE) of the cGMP-binding PDEs. Seven residues are invariant in each A and B regions (see residues indicated by one letter amino acid abbreviations in the "conserved" line of FIG. 3). Residues that are chemically conserved in the A and B regions are indicated by stars in the "conserved" line of FIG. 3. cGMP analog studies of cGB-PDE support the existence of a hydrogen bond between the cyclic nucleotide binding site on cGB-PDE and the 2'OH of cGNP.

Three regions of cGB-PDE have no significant sequence similarity to other PDE isoenzymes. These regions include the sequence flanking the carboxyl-terminal end of the catalytic domain (amino acids 812–875), the sequence separating the cGMP-binding and catalytic domains (amino acids 527–577) and the amino-terminal sequence spanning amino acids 1–141. The site (the serine at position 92 of SEQ ID NO: 10) of phosphorylation of cGB-PDE by cGK is located in this amino-terminal region of sequence. Binding of cGMP to the allosteric site on cGB-PDE is required for its phosphorylation.

A proposed domain structure of cGB-PDE based on the foregoing comparisons with other PDE isoenzymes is presented in FIG. 4. This domain structure is supported by the biochemical studies of cGB-PDE purified from bovine lung.

EXAMPLE 3

The presence of cGB-PDE mRNA in various bovine tissues was examined by Northern blot hybridization.

Polyadenylated RNA was purified from total RNA preparations using the Poly(A) Quick® mRNA purification kit (Stratagene) according to the manufacturer's protocol. RNA samples (5 μg) were loaded onto a 1.2% agarose, 6.7% formaldehyde gel. Electrophoresis and RNA transfer were performed as previously described in Sonnenburg et al., supra. Prehybridization of the RNA blot was carried out for 4 hours at 45° C. in a solution containing 50% formamide, 5× SSC, 25 mM sodium phosphate, pH 7, 2× Denhardt's solution, 10% dextran sulfate, and 0.1 mg/ml yeast tRNA. A random hexanucleotide-primer-labelled probe ($5 \times 10^8$ cpm/μg) was prepared as described in Feinberg et al., supra, using the 4.7 kb cGB-8 cDNA clone of Example 2 excised by digestion with AccI and SacII. The probe was heat denatured and injected into a blotting bag ($6 \times 10^5$ cpm/ml) following prehybridization. The Northern blot was hybridized overnight at 45° C., followed by one 15 minute wash with 2× SSC, 0.1% SDS at room temperature, and three 20 minute washes with 0.1× SSC, 0.1% SDS at 45° C. The blot was exposed to X-ray film for 24 hours at −70° C. The size of the RNA that hybridized with the cGB-PDE probe was estimated using a 0.24–9.5 kb RNA ladder that was stained with ethidium bromide and visuaized with UV light.

The $^{32}$P-labelled cGB-PDE cDNA hybridized to a single 6.8 kb bovine lung RNA species. A mRNA band of the identical size was also detected in polyadenylated RNA isolated from bovine trachea, aorta, kidney and spleen.

EXAMPLE 4

The cGB-PDE cDNA in clone cGB-8 of Example 2 was expressed in COS-7 cells (ATCC CRL1651).

A portion of the cGB-8 cDNA was isolated following digestion with the restriction enzyme XbaI. XbaI cut at a position in the pBluescript polylinker sequence located 30 bp upstream of the 5' end of the cGB-8 insert and at position 3359 within the cGB-8 insert. The resulting 3389 bp fragment, which contains the entire coding region of cGB-8, was then ligated into the unique XbaI cloning site of the expression vector pCDM8 (Invitrogen, San Diego, Calif.). The pCDM8 plasmid is a 4.5 kb eucaryotic expression vector containing a cytomegalovirus promoter and enhancer, an SV40-derived origin of replication, a polyadenylation signal, a procaryotic origin of replication (derived from pBR322) and a procaryotic genetic marker (supF). E. coli MC1061/P3 cells (Invitrogen) were transformed with the resulting ligation products, and transformation positive colonies were screened for proper orientation of the cGB-8 insert using PCR and restriction enzyme analysis. The resulting expression construct containing the cGB-8 insert in the proper orientation is referred to as pCDM8-cGB-PDE.

The pCDM8-cGB-PDE DNA was purified from large-scale plasmid preparations using Qiagen pack-500 columns (Chatsworth, Calif.) according to the manufacturer's protocol. COS-7 cells were cultured in Dulbecco's modified Eagle's medium (DMEM) containing 10% fetal bovine serum, 50 μg/ml penicillin and 50 μg/ml streptomycin at 37° C. in a humidified 5% $CO_2$ atmosphere. Approximately 24 hours prior to transfection, confluent 100 mm dishes of cells were replated at one-fourth or one-fifth the original density. In a typical transfection experiment, cells were washed with buffer containing 137 mM NaCl, 2.7 mM KCl, 1.1 mM potassium phosphate, and 8.1mM sodium phosphate, pH 7.2 (PBS). Then 4–5 ml of DMEM containing 10% NuSerum (Collaborative Biomedical Products, Bedford, Mass.) was added to each plate. Transfection with 10 μg pCDM8-cGB-PDE DNA or pCDM8 vector DNA mixed with 400 μg DEAE-dextran (Pharmacia) in 60 μl TBS [Tris-buffered saline: 25 mM Tris-HCl (pH 7.4), 137 mM NaCl, 5 mM KCl, 0.6 mM $Na_2HPO_4$, 0.7 mM $CaCl_2$, and 0.5 mM $MgCl_2$] was carried out by dropwise addition of the mixture to each plate. The cells were incubated at 37° C., 5% $CO_2$ for 4 hours, and then treated with 10% dimethyl sulfoxide in PBS for 1 minute. After 2 minutes, the dimethyl sulfoxide was removed, the cells were washed with PBS and incubated in complete medium. After 48 hours, cells were suspended in 0.5–1 ml of cold homogenization buffer [40 mM Tris-HCl (pH 7.5), 15 mM benzamidine, 15 mM β-mercaptoethanol, 0.7 μg/ml pepstatin A, 0.5 μg/ml leupeptin, and 5 μM EDTA] per plate of cells, and disrupted using a Dounce homogenizer. The resulting whole-cell extracts were assayed for phosphodiesterase activity, cGMP-binding activity, and total protein concentration as described below in Example 5

EXAMPLE 5

Phosphodiesterase activity in extracts of the transfected COS cells of Example 4 or in extracts of mock transfected COS cells was measured using a modification of the assay procedure described for the cGs-PDE in Martins et al., J. Biol. Chem., 257: 1973–1979 (1982). Cells were harvested and extracts prepared 48 hours after transfection. Incubation mixtures contained 40 mM MOPS buffer (pH 7), 0.8 mM EDTA, 15 mM magnesium acetate, 2 mg/ml bovine serum albumin, 20 μM [$^3$H]cGMP or [$^3$H]cAMP (100,000–200,000 cpm/assay) and COS-7 cell extract in a total volume of 250 μl. The reaction mixture was incubated for 10 minutes at 30° C., and then stopped by boiling. Next, 10 μl of 10mg/ml Crotalus atrox venom (Sigma) was added followed by a 10 minute incubation at 30° C. Nucleoside products were separated from unreacted nucleotides as described in Martins et al., supra. In all studies, less than 15% of the total [$^3$H]cyclic nucleotide was hydrolyzed during the reaction.

Figure 5:
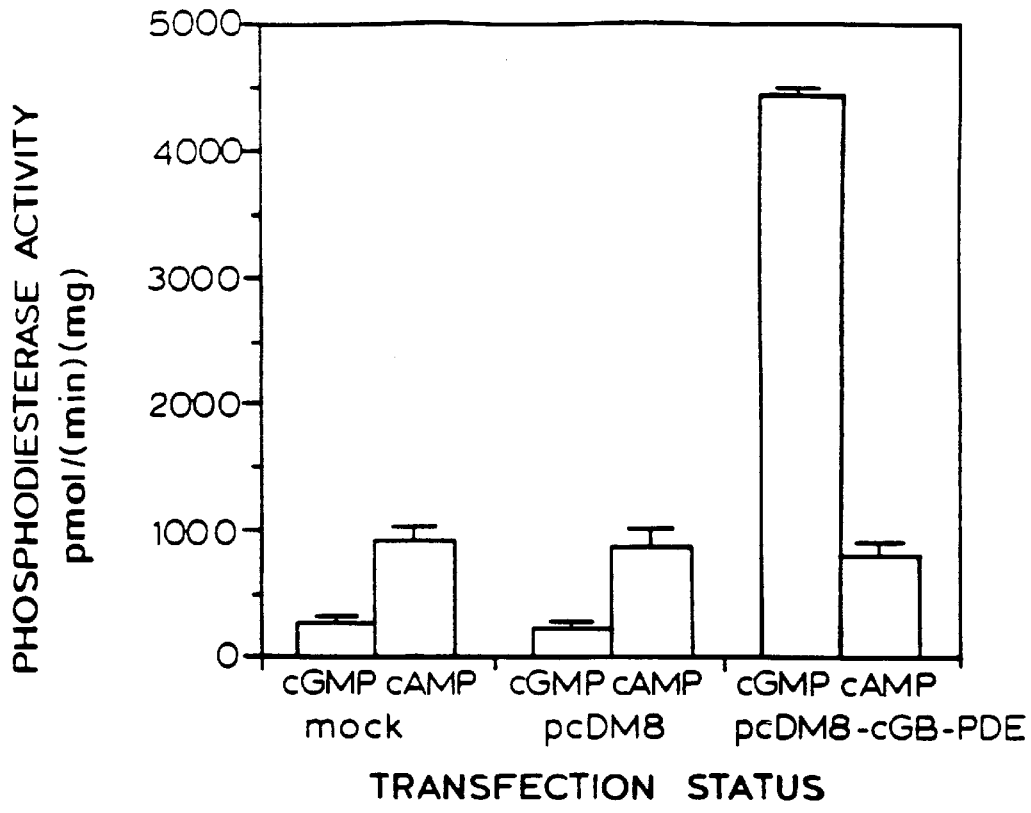
FIG. 5 is a bar graph representing the results of experiments in which extracts of COS cells transfected with bovine cGB-PDE sequences or extracts of untransfected COS cells were assayed for phosphodiesterase activity using either 20 $\mu$M cGMP or 20 $\mu$M cAMP as the substrate.

The results of the assays are presented in FIG. 5 wherein the results shown are averages of three separate transfections. Transfection of COS-7 cells with pCDM8-cGB-PDE DNA resulted in the expression of approximately 15-fold higher levels of cGMP phosphodiesterase activity than in mock-transfected cells or in cells transfected with pCDM8 vector alone. No increase in cAMP phosphodiesterase activity over mock or vector-only transfected cells was detected in extracts from cells transfected with pCDM8-cGB-PDE DNA. These results confirm that the cGB-PDE bovine cDNA encodes a cGMP-specific phosphodiesterase.

Extracts from the transfected COS cells of Example 4 were also assayed for cGMP PDE activity in the presence of a series of concentrations of the PDE inhibitors zaprinast, dipyridamole (Sigma), isobutyl-1-methyl-8-methoxymethyLxanthine (MeOxMeMIX) and rolipram.

Figure 6:
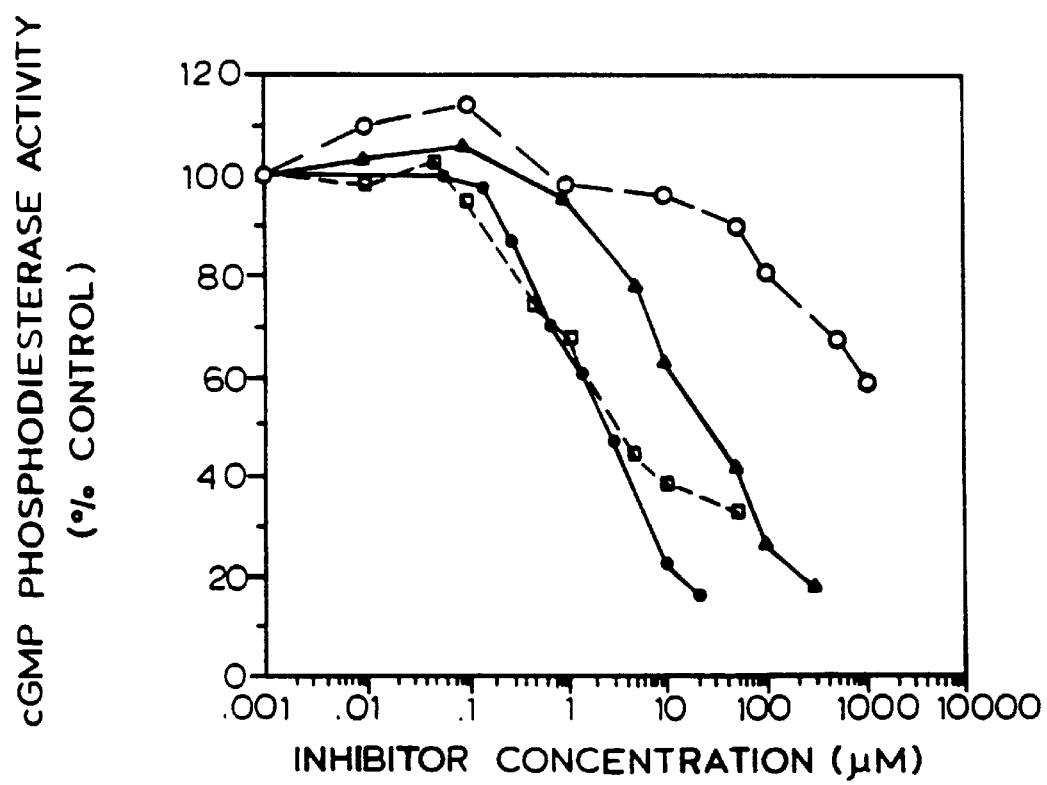
FIG. 6 is a graph depicting results of assays of extracts from cells transfected with bovine cGB-PDE sequences for cGMP phosphodiesterase activity in the presence of a series of concentrations of phosphodiesterase inhibitors including dypyridamole (closed squares), zaprinast (closed circles), methoxymethylxanthine (closed triangles) and rolipram (open circles)

The results of the assays are presented in FIG. 6 wherein PDE activity in the absence of inhibitor is taken as 100% and each data point represents the average of two separate determinations. The relative potencies of PDE inhibitors for inhibition of cGMP hydrolysis by the expressed cGB-BPDE cDNA protein product were identical to those relative potencies reported for native cGB-PDE purified from bovine lung (Thomas I, supra). $IC_{50}$ values calculated from the curves in FIG. 6 are as follows: zaprinast (closed circles), 2 μM; dipyridamole (closed squares), 3.5 μM; MeOxMeMIX (closed triangles), 30 μM; and rolipram (open circles), >300 μM. The $IC_{50}$ value of zaprinast, a relatively specific inhibitor of cGMP-specific phosphodiesterases, was at least two orders of magnitude lower than that reported for inhibition of phosphodiesterase activity of the cGs-PDE or of the cGMP-inhibited phosphodiesterase (cGi-PDEs) (Reeves et al., pp. 300–316 in Beavo et al., supra). Dipyrimadole, an effective inhibitor of selected cAMP- and cGMP-specific phosphodiesterases, was also a potent inhibitor of the expressed cGB-PDE. The relatively selective inhibitor of calcium/calmodulin-stimulated phosphodiesterase (CaM-PDEs), MeOxMeMIX, was approximately 10-fold less potent than zaprinast and dipyridamole, in agreement with results using cGB-PDE activity purified from bovine lung. Rolipram, a potent inhibitor of low $K_m$ cAMP phosphodiesterases, was a poor inhibitor of expressed cGB-PDE cDNA protein product. These results show that the cGB-PDE cDNA encodes a phosphodiesterase that possesses catalytic activity characteristic of cGB-PDE isolated from bovine tissue, thus verifying the identity of the cGB-8 cDNA clone as a cGB-PDE.

It is of interest to note that although the relative potencies of the PDE inhibitors for inhibition of cGMP hydrolysis were identical for the recombinant and bovine isolate cGB-PDE, the absolute $IC_{50}$ values for all inhibitors tested were 2–7 fold higher for the recombinant cGB-PDE. This difference could not be attributed to the effects of any factors present in COS-7 cell extracts on cGMP hydrolytic activity, since cGB-PDE isolated from bovine tissue exhibited identical kinetics of inhibition as a pure enzyme, or when added back to extracts of mock-transfected COS-7 cells. This apparent difference in pharmacological sensitivity may be due to a subtle difference in the structure of the recombinant cGB-PDE cDNA protein product and bovine lung cGB-PDE, such as a difference in post-translational modification at or near the catalytic site. Alternatively, this difference may be due to an alteration of the catalytic activity of bovine lung cGB-PDE over several purification steps.

Cell extracts were assayed for [$^3$H]cGMP-binding activity in the absence or presence of 0.2 mM 3-isobutyl-1-methylxanthine (IBMX) (Sigma), a competitive inhibitor of cGMP hydrolysis. The cGMP binding assay, modified from the assay described in Thomas I, supra, was conducted in a total volume of 80 $\mu$l. Sixty $\mu$l of cell extract was combined with 20 $\mu$l of a binding cocktail such that the final concentration of components of the mixture were 1 $\mu$M [$^3$H]cGMP, 5 $\mu$M cAMP, and 10 $\mu$M 8-bromo-cGMP. The cAMP and 8-bromo-cGMP were added to block [$^3$H]cGMP binding to cAK and cGK, respectively. Assays were carried out in the absence and presence of 0.2 mM IBMX. The reaction was initiated by the addition of the cell extract, and was incubated for 60 minutes at 0° C. Filtration of the reaction mixtures was carried out as described in Thomas I, supra. Blanks were determined by parallel incubations with homogenization buffer replacing cell extracts, or with a 100-fold excess of unlabelled cGMP. Similar results were obtained with both methods. Total protein concentration of the cell extracts was determined by the method of Bradford, Anal. Biochem., 72:248–254 (1976) using bovine serum albumin as the standard.

Figure 7:
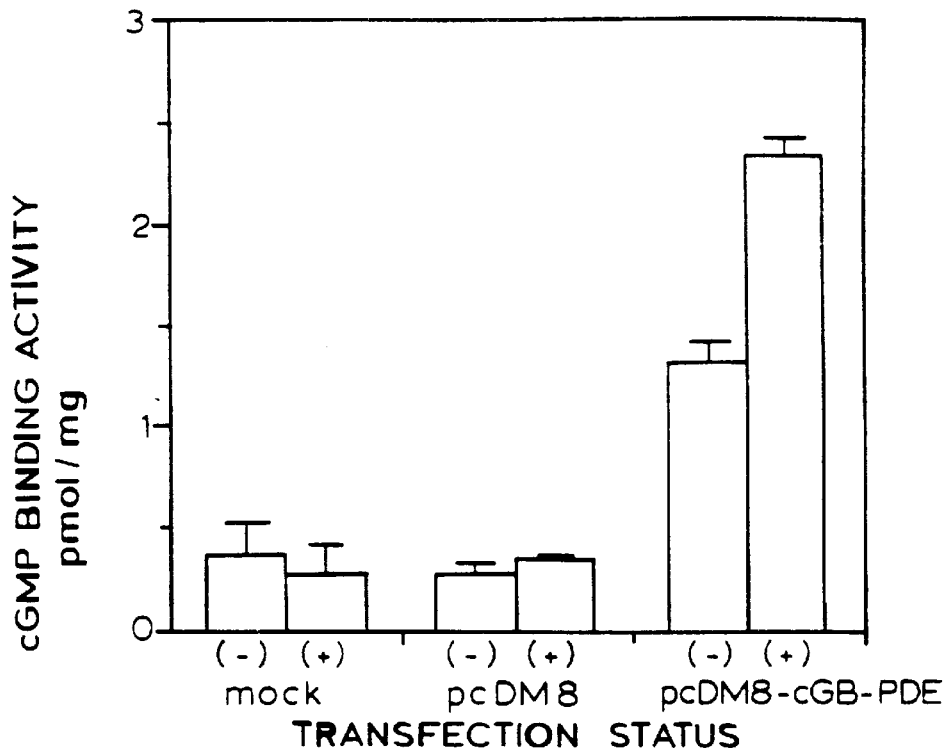
FIG. 7 is a bar graph presenting results of experiments in which cell extracts from COS cells transfected with bovine cGB-PDE sequences or control untransfected COS cells were assayed for [$^3$H]cGMP-binding activity in the absence (−) or presence (+) of 0.2 mM IBMX.

Results of the assay are set out in FIG. 7. When measured at 1 $\mu$M [$^3$H]cGMP in the presence of 0.2 mM IBMX, extracts from COS-7 cells transfected with pCDM8-cGB-PDE exhibited 8-fold higher cGMP-binding activity than extracts from mock-transfected cells. No IBMX stimulation of background cGMP binding was observed suggesting that little or no endogenous cGB-PDE was present in the COS-7 cell extracts. In extracts of pCDM8-cGB-PDE transfected cells cGMP-specific activity was stimulated approximately 1.8-fold by the addition of 0.2 mM IBMX. The ability of IBMX to stimulate cGMP binding 2–5 fold is a distinctive property of the cGMP-binding phosphodisterases.

Figure 8:
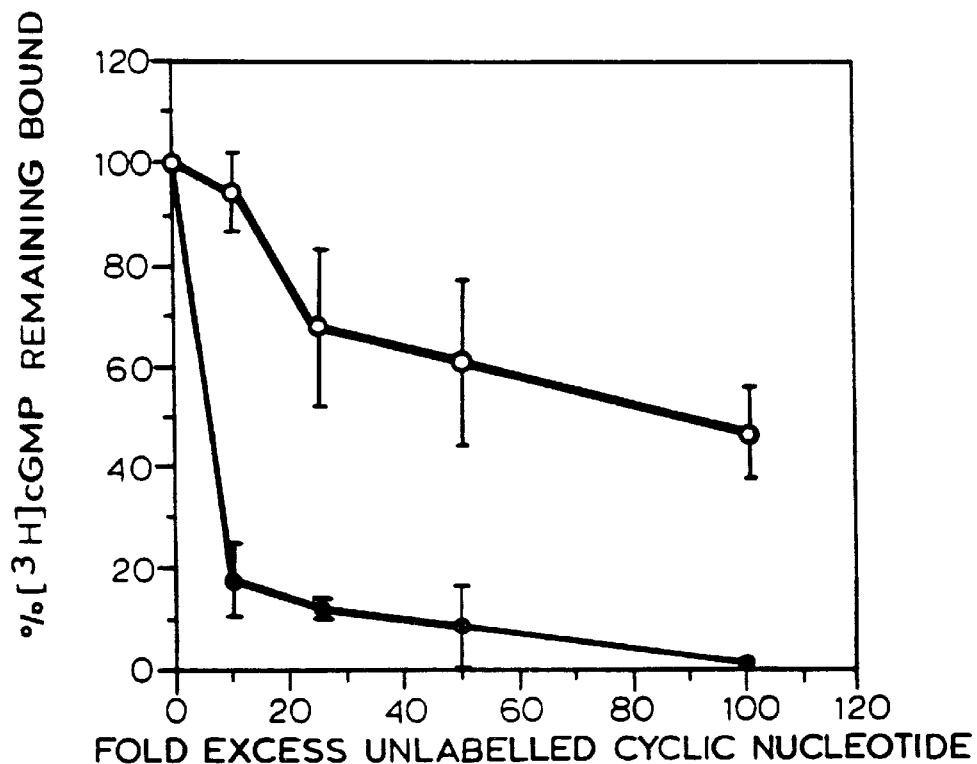
FIG. 8 is a graph of the results of assays in which extracts from cells transfected with bovine cGB-PDE sequences were assayed for [$^3$H]cGMP-binding activity in the presence of excess unlabelled cAMP (open circles) or cGMP (closed circles) at the concentrations indicated.

Cell extracts were assayed as described above for [$^3$H] cGMP-binding activity (wherein concentration of [$^3$H] cGMP was 2.5 $\mu$M) in the presence of excess unlabelled cAMP or cGMP. Results are presented in FIG. 8 wherein cGMP binding in the absence of unlabelled competitor was taken as 100% and each data point represents the average of three separate determinations. The binding activity of the protein product encoded by the cGB-PDE cDNA was specific for cGMP relative to cAMP. Less than 10-fold higher concentrations of unlabelled cGMP were required to inhibit [$^3$H]cGMP binding activity by 50% whereas approximately 100-fold higher concentrations of cAMP were required for the same degree of inhibition.

The results presented in this example show that the cGB-PDE cDNA encodes a phosphodiesterase which possesses biochemical activities characteristic of native cGB-PDE.

The catalytic domains of mammalian PDEs and a Drosophila PDE contain two tandem conserved sequences ($HX_3HX_{24-26}E$) that are typical $Zn^{2+}$-binding motifs in $Zn^{2+}$ hydrolases such as thermolysin [Vallee and Auld, Biochem., 29: 5647–5659 (1990)]. cGB-PDE binds $Zn^{2+}$ in the presence of large excesses of $Mg^{2+}$, $Mn^{2+}$, $Fe^{2+}$, $Fe^{3+}$, $Ca^{22+}$ or $Cd^{2+}$. In the absence of added metal, cGB-PDE has a PDE activity that is approximately 20% of the maximum activity that occurs in the presence of 40 mM $Mg^{2+}$, and this basal activity is inhibited by 1,10-phenanthroline or EDTA. This suggests that a trace metal(s) accounts for the basal PDE activity despite exhaustive treatments to remove metals. PDE activity is stimulated by addition of $Zn^{2+}$ (0.02-1 $\mu$M) or $Co^{2+}$ (1–20 $\mu$M), but not by $Fe^{2+}$, $Fe^{3+}$, $Ca^{2+}$, $Cd^{2+}$, or $Cu^{2+}$. $Zn^{2+}$ increases the basal PDE activity up to 70% of the maximum stimulation produced by 40 mM $Mg^{2+}$. The stimulatory effect of $Zn^{2+}$ in these assays may be compromised by an inhibitory effect that is caused by $Zn^{2+}$ concentrations >1 $\mu$M. The $Zn^{2+}$-supported PDE activity and $Zn^{2+}$ binding by cGB-PDE occur at similar concentrations of $Zn^{2+}$. cGB-PDE thus appears to be a $Zn^{2+}$ hydrolase and $Zn^{2+}$ appears to play a critical role in the activity of the enzyme. See, Colbran et al., The FASEB J., 8: Abstract 2148 (Mar. 15, 1994).

EXAMPLE 6

Several human cDNA clones, homologous to the bovine cDNA clone encoding cGB-PDE, were isolated by hybridization under stringent conditions using a nucleic acid probe corresponding to a portion of the bovine cGB-8 clone (nucleotides 489–1312 of SEQ ID NO: 9).

Isolation of cDNA Fragments Encoding Human cGB-PDE

Three human cDNA libraries (two glioblastoma and one lung) in the vector lambda Zap were probed with the bovine cGB-PDE sequence. The PCR-generated clone corresponding to nucleotides 484–1312 of SEQ ID NO: 9 which is described in Example 1 was digested with EcoRI and SalI and the resulting 0.8 kb cDNA insert was isolated and purified by agarose gel electrophoresis. The fragment was labelled with radioactive nucleotides using a random primed DNA labelling kit (Boehringer).

The cDNA libraries were plated on 150 mm petri plates at a density of approximately 50,000 plaques per plate. Duplicate nitrocellulose filter replicas were prepared. The prehybridization buffer was 3× SSC, 0.1% sarkosyl, 10× Denhardt's, 20 mM sodium phosphate (pH 6.8) and 50

μg/ml salmon testes DNA. Prehybridization was carried out at 65° C. for a minimum of 30 minutes. Hybridization was carried out at 65° C. overnight in buffer of the same composition with the addition of 1–5×10⁵ cpm/ml of probe. The filters were washed at 65° C. in 2× SSC, 0.1% SDS. Hybridizing plaques were detected by autoradiography. The number of cDNAs that hybridized to the bovine probe and the number of cDNAs screened are indicated in Table 2 below.

TABLE 2

| cDNA Library | Type | Positive Plaques | Plaques Screened |
| --- | --- | --- | --- |
| Human SW 1088 glioblastoma | dT-primed | 1 | 1.5 × 10⁶ |
| Human lung | dT-primed | 2 | 1.5 × 10⁶ |
| Human SW 1088 glioblastoma | dT-primed | 4 | 1.5 × 10⁶ |

Plasmids designated cgbS2.1, cgbS3.1, cgbL23.1, cgbL27.1 and cgbS27.1 were excised in vivo from the lambda Zap clones and sequenced.

Clone cgbS3.1 contains 2060 bp of a PDE open reading frame followed by a putative intron. Analysis of clone cgbS2.1 reveals that it corresponds to clone cgbS3.1 positions 664 to 2060 and extends the PDE open reading frame an additional 585 bp before reading into a putative intron. The sequences of the putative 5' untranslated region and the protein encoding portions of the cgbS2.1 and cgbS3.1 clones are set out in SEQ ID NOs: 11 and 12, respectively. Combining the two cDNAs yields a sequence containing approximately 2.7 kb of an open reading encoding a PDE. The three other cDNAs did not extend any further 5' or 3' than cDNA cgbS3.1 or cDNA cgbS2.1.

To isolate additional cDNAs, probes specific for the 5' end of clone cgbS3.1 and the 3' end of clone cgbS2.1 were prepared and used to screen a SW1088 glioblastoma cDNA library and a human aorta cDNA library. A 5' probe was derived from clone cgbS3.1 by PCR using the primers cgbS3.1S311 and cgbL23.1A1286 whose sequences are set out in SEQ ID NOs: 8 and 9, respectively, and below.

Primer cgbS3.1S311 (SEQ ID NO: 13)

5' GCCACCAGAGAAATGGTC 3'

Primer cgbL23.11A1286 (SEQ ID NO: 14)

5' ACAATGGGTCTAAGAGGC 3'

The PCR reaction was carried out in a 50 ul reaction volume containing 50 pg cgbS3.1 cDNA, 0.2 mM dNTP, 10 ug/ml each primer, 50 mM KCl, 10 mM Tris-HCl pH 8.2, 1.5 mM MgCl₂ and Taq polymerase. After an initial four minute denaturation at 94° C., 30 cycles of one minute at 94° C., two minutes at 50° C. and four minutes at 72° C. were carried out. An approximately 0.2 kb fragment was generated by the PCR reaction which corresponded to nucleotides 300–496 of clone cgbS3.1.

A 3' probe was derived from cDNA cgbS2.1 by PCR using the oligos cgbL23.1S1190 and cgbS2.1A231 whose sequences are set out below.

Primer cgbL23.1S1190 (SEQ ID NO: 15)

5' TCAGTGCATGITTGCTGC 3'

Primer cgbS2.1A231 (SEQ ID NO: 16)

5' TACAAACATGTFCATCAG 3'

The PCR reaction as carried out similarly to that described above for generating the 5' probe, and yielded a fragment of approximately 0.8kb corresponding to nucleotides 1358–2139 of cDNA cgbS2.1. The 3' 157 nucleotides of the PCR fragment (not shown in SEQ ID NO: 12) are within the presumptive intron.

The two PCR fragments were purified and isolated by agarose gel electrophoresis, and were labelled with radioactive nucleotides by random priming. A random-primed SW1088 glioblastoma cDNA library (1.5×10⁶ plaques) was screened with the labelled fragments as described above, and 19 hybridizing plaques were isolated. An additional 50 hybridizing plaques were isolated from a human aorta cDNA library (dT and random primed, Clontech, Palo Alto, Calif.).

Plasmids were excised in vivo from some of the positive lambda Zap clones and sequenced. A clone designated cgbS53.2, the sequence of which is set out in SEQ ID NO: 17, contains an approximately 1.1 kb insert whose sequence overlaps the last 61 bp of cgbS3.1 and extends the open reading frame an additional 135 bp beyond that found in cgbS2.1. The clone contains a termination codon and approximately 0.3 kB of putative 3' untranslated sequence. Generation of a Composite cDNA Encoding Human cGB-PDE Clones cgbS3.1, cgbS2.1 and cgbS53.2 were used as described in the following paragraphs to build a composite cDNA that contained a complete human cGB-PDE opening reading frame. The composite cDNA is designated cgbmetls156-2 and was inserted in the yeast ADH1 expression vector pBNY6N.

First, a plasmid designated cgb stop-2 was generated that contained the 3' end of the cGB-PDE open reading frame. A portion of the insert of the plasmid was generated by PCR using clone cgbS53.2 as a template. The PCR primers utilized were cgbS2.1S1700 and cgbstop-2.

Primer cgbS2.1S1700 (SEQ ID NO: 18)

5' TITGGAAGATCCTCATCA 3'

Primer cgbstop-2 (SEQ ID NO: 19)

5' ATGTCTCGAGTCAG' ITCCGCTrGGCCTG 3'

The PCR reaction was carried out in 50 μl containing 50 pg template DNA, 0.2 mM dNTPs, 20 mM Tris-HCl pH 8.2, 10 mM KCl, 6 mM (NH₄)₂SO₄, 1.5 mM MgCl₂, 0.1% Triton-X-100, 500 ng each primer and 0.5 units of Pfu polymerase (Stratagene). The reaction was heated to 94° C. for 4 minutes and then 30 cycles of 1 minute at 94° C., 2 minutes at 50° C. and four minutes at 72° C. were performed. The polymerase was added during the first cycle at 50° C. The resulting PCR product was phenol/chloroform extracted, chloroform extracted, ethanol precipitated and cut with the restriction enzymes BclI and XhoI. The restriction fragment was purified on an agarose gel and eluted.

This fragment was ligated to the cDNA cgbS2.1 that had been grown in dam E. coli, cut with the restriction enzymes BclI and XhoI, and gel-purified using the Promega magic PCR kit. The resulting plasmid was sequenced to verify that cgbstop-2 contains the 3' portion of the cGB-PDE open reading frame, Second, a plasmid carrying the 5' end of the human cGB-PDE open reading frame was generated. Its insert was generated by PCR using clone cgbS3.1 as a template. PCR was performed as described above using primers cgbmet156 and cgbS2.1A2150.

Primer cgbmetl156 (SEQ ID NO: 20)

5' TACAGAATTCTGACCATGGAGCGGGCCGGC 3'

Primer cgbS2.1A2150 (SEQ ID NO: 21)

5' CATTCTAAGCGGATACAG 3'

The resulting PCR fragment was phenol/choloform extracted, choloform extracted, ethanol precipitated and purified on a Sepharose CL-6B column. The fragment was cut with the restriction enzymes EcoRV and EcoRI, run on an agarose gel and purified by spinning through glass wool. Following phenol/chloroform extraction, chloroform extraction and ethanol precipitation, the fragment was ligated into EcoRI/EcoRV digested BluescriptII SK(+) to generate plasmid cgbmet156. The DNA sequence of the insert and junctions was determined. The insert contains a new EcoRI site and an additional 5 nucleotides that together replace the original 155 nucleotides 5' of the initiation codon. The insert extends to an EcoRV site beginning 531 nucleotides from the initiation codon.

The 5' and 3' portions of the cGB-PDE open reading frame were then assembled in vector pBNY6a. The vector pBNY6a was cut with EcoRI and XhoI, isolated from a gel and combined with the agarose gel purified EcoRI/EcoRV fragment from cgbmet156 and the agarose gel purified EcoRV/XhoI fragment from cgbstop-2. The junctions of the insert were sequenced and the construct was named hcbgmet156-2 6a.

The cGB-PDE insert from hcbgmet156-2 6a was then moved into the expression vector pBNY6n. Expression of DNA inserted in this vector is directed from the yeast ADH1 promoter and terminator. The vector contains the yeast 2 micron origin of replication, the pUC19 origin of replication and an ampicillan resistance gene. Vector pBNY6n was cut with EcoRI and XhoI and gel-purified. The EcoRI/XhoI insert from hcgbmet156-2 6a was gel purified using Promega magic PCR columns and ligated into the cut pBNY6n. All new junctions in the resulting construct, hcgbmet156-2 6n, were sequenced. The DNA and deduced amino acid sequences of the insert of hcgbmetl5-2 6n which encodes a composite human cGB-PDE is set out in SEQ ID NOs: 22 and 23. The insert extends from the first methionine in clone cgbS3.1 (nucleotide 156) to the stop codon (nucleotide 2781) in the composite cDNA. Because the methionine is the most 5' methionine in clone cgbS3.1 and because there are no stop codons in frame with the methionine and upstream of it, the insert in pBNY6n may represent a truncated form of the open reading frame.

Variant cDNAs

Four human cGB-PDE cDNAs that are different from the hcgbmet156-2 6n composite cDNA have been isolated. One cDNA, cgbL23.1, is missing an internal region of hcgbmet156-2 6n (nucleotides 997–1000 to 1444–1447). The exact end points of the deletion cannot be determined from the cDNA sequence at those positions. Three of the four variant cDNAs have 5' end sequences that diverge from the hcgbmet156-2 6n sequence upstream of nucleotide 151 (cDNAs cgbA7f, cgbA5C, cgbI2). These cDNAs presumably represent alteratively spliced or unspliced mRNAs.

EXAMPLE 7

The composite human cGB-PDE cDNA construct, hcgbmet156-2 6n, was transformed into the yeast strain YKS45 (ATCC 74225) MATα his3 trp1 ura3 leu3 pde1::HIS3 pde2::TRP1) in which two endogenous PDE genes are deleted. Transformants complementing the leu deficiency of the YKS45 strain were selected and assayed for cGB-PDE activity. Extracts from cells bearing the plasmid hcgbmet156-2 6n were determined to display cyclic GMP-specific phosphodiesterase activity by the assay described below.

One liter of YKS45 cells transformed with the plasmid cgbmet156-2 6n and grown in SC-leu medium to a density of $1-2 \times 10^7$ cells/ml was harvested by centrifugation, washed once with deionized water, frozen in dry ice/ethanol and stored at $-70°$ C. Cell pellets (1–1.5 ml) were thawed on ice in the presence of an equal volume of 25 mM Tris-Cl (pH 8.0)/5 mM EDTA/5 mM EGTA/1 mM o-phenanthroline/0.5 mM AEBSF (Calbiochem)/0.1% β-mercaptoethanol and 10 ug/ml each of aprotinin, leupeptin, and pepstatin A. The thawed cells were added to 2 ml of acid-washed glass beads (425–600 μM, Sigma) in 15 ml Corex tube. Cells were broken with 4 cycles consisting of a 30 second vortexing on setting 1 followed by a 60 second incubation on ice. The cell lysate was centrifuged at 12,000×g for 10 minutes and the supernatant was passed through a 0.8 a filter. The supernatant was assayed for cGMP PDE activity as follows. Samples were incubated for 20 minutes at 30° C. in the presence of 45 mM Tris-Cl (pH 8.0), 2 mM EGTA, lmM EDTA, 0.2 mg/ml BSA, 5 mM $MgCl_2$, 0.2 mM o-phenanthroline, 2 ug/ml each of pepstatin A, leupeptin, and aprotinin, 0.1 mM AEBSF, 0.02% βmercaptoethanol and 0.1 mM [$^3$H]cGMP as substrate. [$^{14}$C]-AMP (0.5 nCi/assay) was added as a recovery standard. The reaction was terminated with stop buffer (0.1M ethanolamine pH 9.0, 0.5M ammonium sulfate, 10 mM EDTA, 0.05% SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25 acetic acid and mixed with 5 ml Ecolume (ICN Biochemicals). The radioactive product was measured by scintillation counting.

EXAMPLE 8

Analysis of expression of cGB-PDE mRNA in human tissues was carried out by RNase protection assay.

A probe corresponding to a portion of the putative cGMP binding domain of cGB-PDE (402 bp corresponding to nucleotides 1450 through 1851 of SEQ ID NO: 13) was generated by PCR. The PCR fragment was inserted into the EcoRI site of the plasmid pBSII SK(−) to generate the plasmid RP3. RP3 plasmid DNA was linearized with XbaI and antisense probes were generated by a modification of the Stratagene T7 RNA polymerase kit. Twenty-five ng of linearized plasmid was combined with 20 microcuries of alpha $^{32}$P rUTP (800 Ci/mmol, 10 mCi/ml), 1× transcription buffer (40 mM TrisCl, pH 8, 8mM $MgCl_2$, 2 mM spermidine, 50 mM NaCl), 0.25 mM each rATP, rGTP and rCTP, 0.1 units of RNase Block II, 5 mM DTT, 8 μM rUTP and 5 units of T7 RNA Polymerase in a total volume of 5 μl. The reaction was allowed to proceed 1 hour at room temperature and then the DNA template was removed by digestion with RNase free DNase. The reaction was diluted into 100 μl of 40 mM TrisCl, pH 8, 6 mM $MgCl_2$ and 10 mM NaCl. Five units of RNase-free DNase were added and the reaction was allowed to continue another 15 minutes at 37° C. The reaction was stopped by a phenol extraction followed by a phenol chloroform extraction. One half volume of 7.5M $NH_4OAc$ was added and the probe was ethanol precipitated.

The RNase protection assays were carried out using the Ambion RNase Protection kit (Austin, Tex.) and 10 μg RNA isolated from human tissues by an acid guanidinium extraction method. Expression of cGB-PDE mRNA was easily detected in RNA extracted from skeletal muscle, uterus, bronchus, skin, right saphenous vein, aorta and SW1088 glioblastoma cells. Barely detectable expression was found in RNA extracted from right atrium, right ventricle, kidney cortex, and kidney medulla. Only complete protection of the RP3 probe was seen. The lack of partial protection argues against the cDNA cgbL23.1 (a variant cDNA described in Example 7) representing a major transcript, at least in these RNA samples.

EXAMPLE 9

Polyclonal antisera was raised to E. coli-produced fragments of the human cGB-PDE.

A portion of the human cGB-PDE cDNA (nucleotides 1668–2612 of SEQ ID NO: 22, amino acids 515–819 of SEQ ID NO: 23) was amplified by PCR and inserted into the E. coli expression vector pGEX2T (Pharmacia) as a BamHI/EcoRI fragment. The pGEX2T plasmid carries an ampicillin resistance gene, an E. coli laq $I^q$ gene and a portion of the Schistosoma japonicum glutathione-S-transferase (GST) gene. DNA inserted in the plasmid can be expressed as a fusion protein with GST and can then be cleaved from the GST portion of the protein with thrombin. The resulting plasmid, designated cgbPE3, was transformed into E. coli strain LE392 (Stratagene). Transformed cells were grown at 37° C. to an OD600 of 0.6. IPTG (isopropylthioalactopyranoside) was added to 0.1 mM and the cells were grown at 37° C. for an additional 2 hours. The cells were collected by centrifmgation and lysed by sonication. Cell debris was removed by centrifugation and the supernatant was fractionated by SDS-PAGE. The gel was stained with cold 0.4M KCl and the GST-cgb fusion protein band was excised and electroeluted. The PDE portion of the protein was separated from the GST portion by digestion with thrombin. The digest was fractionated by SDS-PAGE, the PDE protein was electroeluted and injected subcutaneously into a rabbit. The resultant antisera recognizes both the bovine cGB-PDE fragment that was utilized as antigen and the full length human cGB-PDE protein expressed in yeast (see Example 8).

EXAMPLE 10

Polynucleotides encoding various cGB-PDE analogs and cGB-PDE fragments were generated by standard methods.

A. cGB-PDE Analogs

All known cGMP-binding PDEs contain two internally homologous tandem repeats within their putative cGMP-binding domains. In the bovine cGB-PDE of the invention, the repeats span at least residues 228–311 (repeat A) and 410–500 (repeat B) of SEQ ID NO: 10. Site-directed mutagenesis of an aspartic acid that is conserved in repeats A and B of all known cGMP-binding PDEs was used to create analogs of cGB-PDE having either Asp-289 replaced with Ala (D289A) or Asp-478 replaced with Ala (D478A). Recombinant wild type (WT) bovine and mutant bovine cGB-PDEs were expressed in COS-7 cells. cGB-PDE purified from bovine lung (native cGB-PDE) and WT cGB-PDE displayed identical cGMP-binding kdnetics with a $K_d$ of approximately 2 $\mu$M and a curvilinear dissociation profile ($t_{1/2}$=1.3 hours at 4° C). This curvilinearity may have been due to the presence of distinct high affiity (slow) and low affinity (fast) sites of cGMP binding. The D289A mutant had significantly decreased affinity for cGMP ($K_d$>20 $\mu$M) and a single rate of cGMP-association ($t_{1/2}$=0.5 hours), that was similar to that calculated for the fast site of WT and native cGB-PDE. This suggested the loss of a slow cGMP-binding site in repeat A of this mutant. Conversely, the D478A mutant showed higher affinity for cGMP ($K_d$ of approximately 0.5 $\mu$M) and a single cGMP-dissociation rate ($t_{1/2}$= 2.8 hours) that was similar to the calculated rate of the slow site of WT and native cGB-PDE. This suggested the loss of a fast site when repeat B was modified. These results indicate that dimeric cGB-PDE possesses two homologous but kinetically distinct cGMP-binding sites, with the conserved aspartic acid being critical for interaction with cGMP at each site. See, Colbran et al., FASEB J., 8: Abstract 2149 (May 15, 1994).

B. Amino-Terminal Truncated cGB-PDE Polypeptides

A truncated human cGB-PDE polypeptide including amino acids 516–875 of SEQ ID NO: 23 was expressed in yeast. A cDNA insert extending from the NcoI site at nucleotide 1555 of SEQ ID NO: 22 through the XhoI site at the 3' end of SEQ ID NO: 22 was inserted into the ADH2 yeast expression vector YEpC-PADH2d [Price et al., Meth. Enymol., 185: 308–318 (1990)] that had been digested with NcoI and SalI to generate plasmid YEpC-PADH2d HcGB. The plasmid was transformed into spheroplasts of the yeast strain yBJ2-54 (prcl-407 prb1-1122 pep4-3 leu2 trp1 ura3-52 Δpde1:URA3, HIS3 Δpde2::TRP1 cir•). The endogenous PDE genes are deleted in this strain. Cells were grown in SC-leu media with 2% glucose to $10^7$ cells/ml, collected by filtration and grown 24 hours in YEP media containing 3% glycerol. Cells were pelleted by centrifugation and stored frozen. Cells were disrupted with glass beads and the cell homogenate was assayed for phosphodiesterase activity essentially as described in Prpic et al., Anal. Biochem., 208: 155–160 (1993). The truncated human cGB-PDE polypeptide exhibited phosphodiesterase activity.

C. Carboxy-Terminal Truncated cGB-PDE Polypeptides

Two different plasmids encoding carboxy-terminal truncated human cGB-PDE polypeptides were constructed.

Plasmid pBJ6-84Hin contains a cDNA encoding amino acids 1–494 of SEQ ID NO: 23 inserted into the NcoI and SalI sites of vector YEpC-PADH2d. The cDNA insert extends from the NcoI site at nucleotide position 10 of SEQ ID NO: 22 through the HindIII site at nucleotide position 1494 of SEQ ID NO: 22 followed by a linker and the SalI site of YEpC-PADH2d.

Plasmid pBJ6–84Ban contains a cDNA encoding amino acids 1-549 of SEQ ID NO: 23 inserted into the NcoI and SalI sites of vector YEpC-PADH2d. The cDNA insert extends from the NcoI site at nucleotide position 10 of SEQ ID NO: 22 through the BanI site at nucleotide position 1657 bf SEQ ID NO: 22 followed by a linker and the SalI site of YEpC-PADH2d.

The trucated cGB-PDE polypeptides are useful for screening for modulators of cGB-PDE activity.

EXAMPLE 11

Monoclonal antibodies reactive with human cGB-PDE were generated.

Yeast yBJ2-54 containing theplasmid YEpADH2HcGB (Example 10B) were fermented in a New Brunswick Scientific 10 liter Microferm. The cGB-PDE cDNA insert in plasmid YEpADH2 HcGB extends from the NcoI site at nucleotide 12 of SEQ ID NO: 22 to the XhoI site at the 3' end of SEQ ID NO: 22. An inoculum of $4 \times 10^9$ cells was added to 8 liters of media containing SC-leu, 5% glucose, trace metals, and trace vitamins. Fermentation was maintained at 26° C., agitated at 600 rpm with the standard microbial impeller, and aerated with compressed air at 10 volumes per minute. When glucose decreased to 0.3% at 24 hours post-inoculation the culture was infused with 2 liters of 5× YEP media containing 15% glycerol. At 66 hours post-inoculation the yeast from the ferment was harvested by centrifugation at 4,000× g for 30 minutes at 4° C. Total yield of biomass from this fermentation approached 350 g wet weight.

Human cGB-PDE enzyme was purified from the yeast cell pellet. Assays for PDE activity using 1 mM cGMP as substrate was employed to follow the chromatography of the enzyme. All chromatographic manipulations were performed at4° C.

Yeast (29g. wet weight) were resuspended in 70ml of buffer A (25 mM Tris pH 8.0, 0.25 mM DTT, 5 mM $MgCl_2$, 10 μM ZnSO4, 1 mM benzamidine) and lysed by passing through a microfluidizer at 22–24,000 psi. The lysate was centrifuged at 10,000×g for 30 minutes and the supernatant was applied to a 2.6×28 cm column containing Pharmacia Fast Flow Q anion exchange resin equilibrated with buffer B containing 20 mM BisTris-propane pH 6.8, 0.25 mM DTT, 1 mM MgCl$_2$, and 10 μM ZnSO$_4$. The column was washed with 5 column volumes of buffer B containing 0.125M NaCl and then developed with a linear gradient from 0.125 to 1.0M NaCl. Fractions containing the enzyme were pooled and applied directly to a 5×20 cm column of ceramic hydroxyapatite (BioRad) equilibrated in buffer C containing 20 mM BisTris-propane pH 6.8, 0.25 mM DIT, 0.25MKCl, 1 mM MgCl$_2$, and 10 μM ZnSO$_4$. The column was washed with 5 column volumes of buffer C and eluted with a linear gradient from 0 to 250 mM potassium phosphate in buffer C. The pooled enzyme was concentrated 8-fold by ultrafiltration (YM30 membrane, Amicon). The concentrated enzyme was chromatographed on a 2.6×90 cm column of Pharmacia Sephacryl S300 (Piscataway, N.J.) equilibrated in 25 mM BisTris-propane pH 6.8, 0.25 mM DTT, 0.25M NaCl, 1 mM MgCl$_2$, and 20 μM ZnSO$_4$. Approximately 4 mg of protein was obtained. The recombinant human cGB-PDE enzyme accounted for approximately 90% of protein obtained as judged by SDS polyacrylamide gel electrophoresis followed by Coomassie blue staining.

The purified protein was used as an antigen to raise monoclonal antibodies. Each of 19 week old Balblc mice (Charles River Biotechnical Services, Inc., Wilmington, Mass.) was immunized sub-cutaneously with 50 ug purified human cGB-PDE enzyme in a 200 ul emulsion consisting of 50% Freund's complete adjuvant (Sigma Chemical Co.). Subsequent boosts on day 20 and day 43 were administered in incomplete Freund's adjuvant. A pre-fusion boost was done on day 86 using 50 ug enzyme in PBS. The fusion was performed on day 90.

The spleen from mouse #1817 was removed sterilely and placed in 10 ml serum free RPMI 1640. A single-cell suspension was formed and filtered through sterile 70-mesh Nitex cell strainer (Becton Dicldnson, Parsippany, N.J.), and washed twice by centrifuging at 200 g for 5 minutes and resuspending the pellet in 20 ml serum free RPMI. Thymocytes taken from 3 naive Balb/c mice were prepared in a similar manner.

NS-1 myeloma cells, kept in log phase in RPMI with 11% Fetalclone (FBS) (Hyclone Laboratories, Inc., Logan, Utah) for three days prior to fusion, were centrifuged at 200 g for 5 minutes, and the pellet was washed twice as described in the foregoing paragraph. After washing, each cell suspension was brought to a final volume of 10 ml in serum free RPMI, and 20 μl was diluted 1:50 in 1 ml serum free RPMI. 20 μl of each dilution was removed, mixed with 20 μl 0.4% trypan blue stain in 0.85% saline (Gibco), loaded onto a hemocytometer (Baxter Healthcare Corp., Deerfield, Ill.) and counted.

Two × 10$^8$ spleen cells were combined with 4.0×10$^7$ NS-1 cells, centrifuged and the supernatant was aspirated. The cell pellet was dislodged by tapping the tube and 2 ml of 37° C. PEG 1500 (50% in 75 mM Hepes, pH 8.0) (Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 μM sodium hypoxanthine, 0.4 μM aminopterin, 16 μM thymidine (HAT) (Gibco), 25 units/ml IL-6 (Boehringer Mannheim) and 1.5× 10$^6$ thymocytes/ml. The suspension was first placed in a T225 flask (Corning, United Kingdom) at 37° C. for two hours before being dispensed into ten 96-well flat bottom tissue culture plates (Corning, United Kingdom) at 200 μl/well. Cells in plates were fed on days 3, 4, 5 post fusion day by aspirating approximately 100 μl from each well with an 20 G needle (Becton Dickinson), and adding 100 μl/well plating medium described above except containing 10 units/ml IL-6 and lacking thymocytes.

The fusion was screened initially by ELISA. Immulon 4 plates (Dynatech) were coated at 4° C. overnight with purified recombinant human cGB-PDE enzyme (100 ng/well in 50 mM carbonate buffer pH9.6). The plates were washed 3× with PBS containing 0.05% Tween 20 (PBSI). The supernatants from the individual hybridoma wells were added to the enzyme coated wells (50 μl/well). After incubation at 37° C. for 30 minutes, and washing as above, 50 μl of horseradish peroxidase conjugated goat anti-mouse IgG(fc) (Jackson ImmunoResearch, West Grove, Pa.) diluted 1:3500 in PBST was added. Plates were incubated as above, washed 4× with PBST and 100 μl substrate consisting of 1 mg/ml o-phenylene diamine (Sigma) and 0.1 μl/ml 30% H$_2$O$_2$ in 100 mM citrate, pH 4.5, was added. The color reaction was stopped in 5 minutes with the addition of 50 μl of 15% H$_2$SO$_4$. A$_{490}$ was read on a plate reader (Dynatech).

Wells C5G, E4D, F1G, F9H, F11G, J4A, and J5D were picked and renamed 102A, 102B, 102C, 102D, 102E, 102F, and 102G respectively, cloned two or three times, successively, by doubling dilution in RPMI, 15% FBS, 100 μM sodium hypoxanthine, 16 μM thymidine, and 10 units/ml IL-6. Wells of clone plates were scored visually after 4 days and the number of colonies in the least dense wells were recorded. Selected wells of the each cloning were tested by ELISA.

The monoclonal antibodies produced by above hybridomas were isotpped in an ELISA assay. Results showed that monoclonal antibodies 102A to 102E were IgG1, 102F was IgG2b and 102G was IgG2a.

All seven monoclonal antibodies reacted with human cGS-PDE as determined by Western analysis.

EXAMPLE 12

Developing modulators of the biological activities of specific PDEs requires differentiating PDE isozymes present in a particular assay preparation. The classical enzymological approach of isolating PDEs from natural tissue sources and studying each new isozyme is hampered by the limits of purification techniques and the inability to definitively assess whether complete resolution of a isozyme has been achieved. Another approach has been to identify assay conditions which might favor the contribution of one isozyme and minimize the contribution of others in a preparation. Still another approach has been the separation of PDEs by immunological means. Each of the foregoing approaches for differentiating PDE isozymes is time consuming and technically difficult. As a result many attempts to develop selective PDE modulators have been performed with preparations containing more than one isozyme. Moreover, PDE preparations from natural tissue sources are susceptible to limited proteolysis and may contain mixtures of active proteolytic products that have different kinetic, regulatory and physiological properties than the full length PDEs.

Recombinant cGB-PDE polypeptide products of the invention greatly facilitate the development of new and specific cGB-PDE modulators. The use of human recombinant enzymes for screening for modulators has many inherent advantages. The need for purification of an isozyme can be avoided by expressing it recombinantly in a host cell that lacks endogenous phosphodiesterase activity (e.g., yeast strain YKS45 deposited as ATCC 74225). Screening compounds against human protein avoids complications that often arise from screening against non-human protein where a compound optimized on a non-human protein may fail to be specific for or react with the human protein. For example, a single amino acid difference between the human and rodent $5HT_{1B}$ serotonin receptors accounts for the difference in binding of a compound to the receptors. [See Oskenberg et al., Nature,360: 161–163 (1992)]. Once a compound that modulates the activity of the cGB-PDE is discovered, its selectivity can be evaluated by comparing its activity on the cGB-PDE to its activity on other PDE isozymes. Thus, the combination of the recombinant cGB-PDE products of the invention with other recombinant PDE products in a series of independent assays provides a system for developing selective modulators of cGB-PDE. Selective modulators may include, for example, antibodies and other proteins or peptides which specifically bind to the cGB-PDE or cGB-PDE nucleic acid, oligonucleotides which specifically bind to the cGB-PDE (see Patent Cooperation Treaty International Publication No. WO93/05182 published Mar. 18, 1993 which describes methods for selecting oligonucleotides which selectively bind to target biomolecules) or cGB-PDE nucleic acid (e.g., antisense oligonucleotides) and other non-peptide natural or synthetic compounds which specifically bind to the cGB-PDE or cGB-PDE nucleic acid. Mutant forms of the cGB-PDE which alter the enzymatic activity of the cGB-PDE or its localization in a cell are also contemplated. Crystallization of recombinant cGB-PDE alone and bound to a modulator, analysis of atomic structure by X-ray crystallography, and computer modelling of those structures are methods useful for designing and optimizing non-peptide selective modulators. See, for example, Erickson et al., Ann. Rep. Med. Chem., 27: 271–289 (1992) for a general review of structure-based drug design.

Targets for the development of selective modulators include, for example: (1) the regions of the cGB-PDE which contact other proteins and/or localize the cGB-PDE within a cell, (2) the regions of the cGB-PDE which bind substrate, (3) the allosteric cGMP-binding site(s) of cGB-PDE, (4) the metal-binding regions of the cGB-PDE, (5) the phosphorylation site(s) of cGB-PDE and (6) the regions of the cGB-PDE which are involved in dimerization of cGB-PDE subunits.

While the present invention has been described in terms of specific embodiments, it is understood that variations and modifications will occur to those skilled in the art. Accordingly, only such limitations as appear in the appended claims should be placed on the invention.

We claim:

1. An antibody specifically immunoreactive with the cGMP-binding, cGMP-stimulated phosphodiesterase as set forth in SEQ ID NO: 10.

2. An antibody according to claim 1 which is a monoclonal antibody.

3. A hybridoma cell line producing the monoclonal antibody according to claim 2.

4. An antibody according to claim 1 which is a humanized antibody.

5. An antibody specifically immunoreactive with the cGMP-binding, cGMP-stimulated phosphodiesterase as set forth in SEQ ID NO: 23.

6. An antibody according to claim 5 which is a monoclonal antibody.

7. A hybridoma cell line producing the antibody of claim 6.

8. An antibody according to claim 5 which is a humanized antibody.

* * * * *